United States Patent [19]

Thibado et al.

[11] Patent Number: 5,262,943
[45] Date of Patent: Nov. 16, 1993

[54] SYSTEM AND PROCESS FOR INFORMATION MANAGEMENT AND REPORTING

[75] Inventors: Michael J. Thibado, Excelsior; Dennis P. Morrison, Minnetonka; Dean R. Nichols, Chaska, all of Minn.

[73] Assignee: National Computer Systems, Inc., Minneapolis, Minn.

[21] Appl. No.: 777,650

[22] Filed: Oct. 15, 1991

[51] Int. Cl.$^5$ ...................... G06F 15/00; G06F 15/20
[52] U.S. Cl. ................................ 364/413.01; 395/140
[58] Field of Search ...................... 364/413.01, 413.02; 395/140, 157, 161; 340/722, 752, 753

[56] References Cited

U.S. PATENT DOCUMENTS 4,878,175 10/1989 Norden-Paul et al. ........ 364/413.01
5,072,383 12/1991 Brimm et al. ................. 364/413.01
5,105,354 4/1992 Nishimura ..................... 364/413.03

OTHER PUBLICATIONS

Aileen Kantor, *Researchers Cautious About Outcomes Software Products*, 1 Report on Medical Guidelines & Outcomes Research 9-12 (Oct. 1, 1990).

*Primary Examiner*—Donald E. McElheny, Jr.
*Assistant Examiner*—Khai Tran
*Attorney, Agent, or Firm*—Merchant, Gould, Smith, Edell, Welter & Schmidt

[57] ABSTRACT

The present invention is a system that manages patient information and assessment information associated with those patients. The system maintains a list of patient records and links those patient records with assessment records. The present invention further utilizes assessment processing and reporting rules for managing, analyzing, and generating reports of assessment information. In a preferred embodiment, the reports are displayed by an efficient method of displaying repeated measures data, to assist a user in managing and objectively analyzing a patient's treatment.

56 Claims, 36 Drawing Sheets

© 1991 NATIONAL COMPUTER SYSTEMS, INC.

© 1991 NATIONAL COMPUTER SYSTEMS, INC.

© 1991 NATIONAL COMPUTER SYSTEMS, INC.

© 1991 NATIONAL COMPUTER SYSTEMS, INC.

© 1991 NATIONAL COMPUTER SYSTEMS, INC.

SYSTEM AND PROCESS FOR INFORMATION MANAGEMENT AND REPORTING

FIELD OF THE INVENTION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

The present invention relates to a data processing system for managing and analyzing assessment information. The present invention is particularly useful for, but not limited to, analyzing and managing assessments of patients in the mental health care industry.

BACKGROUND OF THE INVENTION

The health care industry and other fields face many challenges due to the increasing cost of health care and the complexities involved in managing these costs. The industry must strive to provide the best available health care while controlling and managing the costs of providing that care. Since the costs of health care are often established by third-party payers such as insurance companies, the option of increasing the cost of services provided is not always available to health care providers. Therefore, the health care industry must focus on controlling operating costs to maintain a profitable business.

The mental health care field in particular faces many challenges to the management of the traditional therapeutic setting. In a typical environment of a therapist's treatment of a patient, the therapist will record observations, in narrative form, regarding the patient's progress and response to treatment. While this method may be of value to the therapist's treatment strategy, it also may be subjective and thus not provide for objective feedback. Furthermore, comparing how two different patients respond to treatment from two different therapists may be very difficult when both therapists use this method of recording the patient's progress.

There is a need in the health care industry for systems that manage health care and result in an efficient health care strategy for managing costs. These systems will provide, among other things, efficient admission of patients, accurate diagnosis of patient needs, and application of effective proven treatment.

There is in particular a need in the mental health care field for a system that applies objective standards to patient treatment in order to provide documentation of a patient's progress and the effectiveness of treatment. This documentation may, for example, be valuable to insurance companies in order to justify the coverage of treatment under an insurance policy. This documentation may also provide objective analysis of treatment so that a patient may be matched with the most effective type of treatment.

There is a further need in the mental health care field for efficient methods of objectively tracking a patient's progress. Fulfilling all of these needs will assist the mental health care industry to manage the treatment of patients and control costs of treatment.

The present assessment and information display inventions solve these and other shortcomings of the prior art described above. The present assessment and information display inventions also solve other shortcomings of the prior art which will become apparent to those skilled in the art upon reading and understanding the present specification.

SUMMARY OF THE INVENTION

The present assessment invention is a system that manages patient information and assessments associated with those patients. The system maintains a list of patient records and links those patient records with assessment records. The present assessment invention further utilizes assessment processing rules for generating reports of assessments. In a preferred embodiment, the reports are displayed by an efficient method of displaying repeated measures data to assist a user in managing and objectively analyzing a patient's treatment.

The present information display invention is a method of displaying multidimensional repeated measures data to best facilitate visual analysis of the data by showing how the data changes with respect to a first, or baseline, data point for each dimension measured. The method displays the baseline perpendicular to a first axis with the baseline intersecting the first axis at a point equal to a value of the first data point along the first axis.

BRIEF DESCRIPTION OF THE DRAWINGS

In the drawings where like numerals refer to like components throughout several views.

DETAILED DESCRIPTION OF THE PREFERRED EMBODIMENT

In the following detailed description of the preferred embodiment, reference is made to the accompanying drawings which form a part hereof and in which is shown by way of illustration a specific embodiment in which the invention may be practiced. This embodiment is described in sufficient detail to enable those skilled in the art to practice the invention, and it is to be understood that other embodiments may be utilized and that structural or logical changes may be made without departing from the scope of the present invention. The following detailed description is, therefore, not to be taken in a limiting sense, and the scope of the present invention is defined by the appended claims.

I. Overview of the System

The present invention is a system for managing client information, including information which identifies and characterizes the client. In a preferred use of the system, the client is a patient, and the system will assist a clinician in the evaluation and tracking of the patient's progress in a treatment setting. The system therefore provides for a method of measuring the effectiveness of treatment. The system organizes patient information in a series of patient records. The patient records contain background information for a patient and are also linked to one or more assessment records.

As is further explained below, the assessment records typically contain objective and subjective raw data, which is derived from measurement tools, regarding an evaluation of a patient's progress in treatment. This raw data is referred to as "assessment information." The measurement tools used to obtain the assessment information may include standardized tests as well as a therapist's subjective evaluations of a patient. The system may also generate reports by accessing the patient records and assessment records, retrieving assessment information from the assessment records, and processing the assessment information. This processed assessment information, which is used in generating a report, is referred to as an "assessment." Preferred reports provide a graphical representation of the patient's progress based on standardized assessment tools to measure the effectiveness of the patient's treatment.

A preferred embodiment operates as a C language implementation on a PC DOS-based hardware platform operating as a Microsoft Windows application having a revision of 3.0 or greater. One skilled in the art will recognize that other programming, hardware, or windows environments may be used without departing from the scope of the invention.

II. System Modules

A. Platform and Executables

Figure 1A:
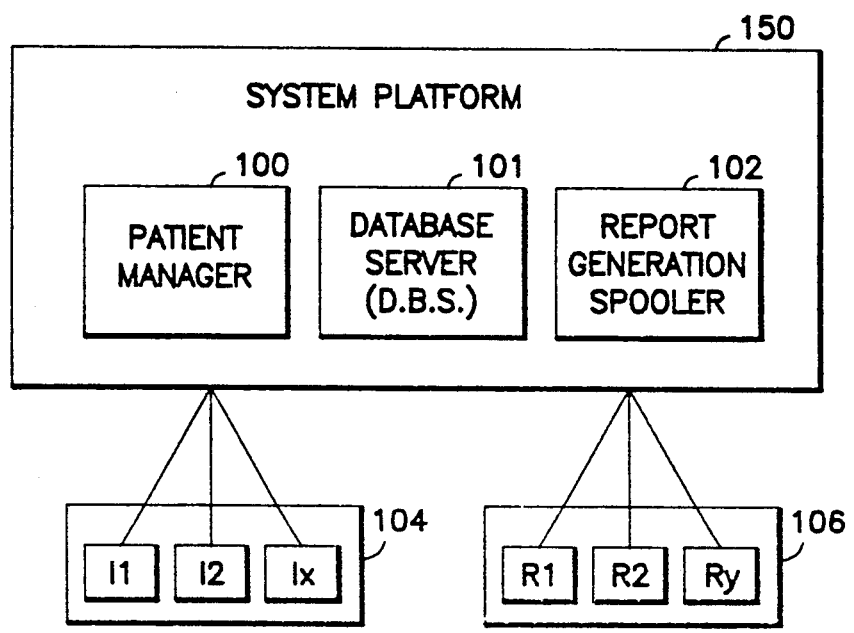
FIG. 1A is a block diagram of a preferred system that implements the present invention.

A preferred system will typically consist of a platform 150 of three modules as shown in FIG. 1A: Patient Manager 100; Database Server 101; and Report Generation Spooler 102. Preferred system platform 150 points to one or more instrument executable programs 104, which will typically be a sub-system operating on one or more patient tests. In a preferred embodiment, these may be various psychological tests such as the SF-36D or Minnesota Multiphasic Personality Inventory ("MMPI"). The instrument executables would also store the test definitions for the various tests on which the system operates. The Database Server 101 stores the actual raw test data (assessment information) on which the executables operate in a database record or structure referred to as "assessment records."

Therefore, each instrument executable is a sub-system tailored to the specific requirements of each set of tests. The system platform 150 may also access one or more report executable sub-systems 106 (Report Module). Each test may contain different amounts or types of data, and the report generation sub-systems 106 in the Report Module must be tailored to the specific parameters of the data for each test.

Figure 1B:
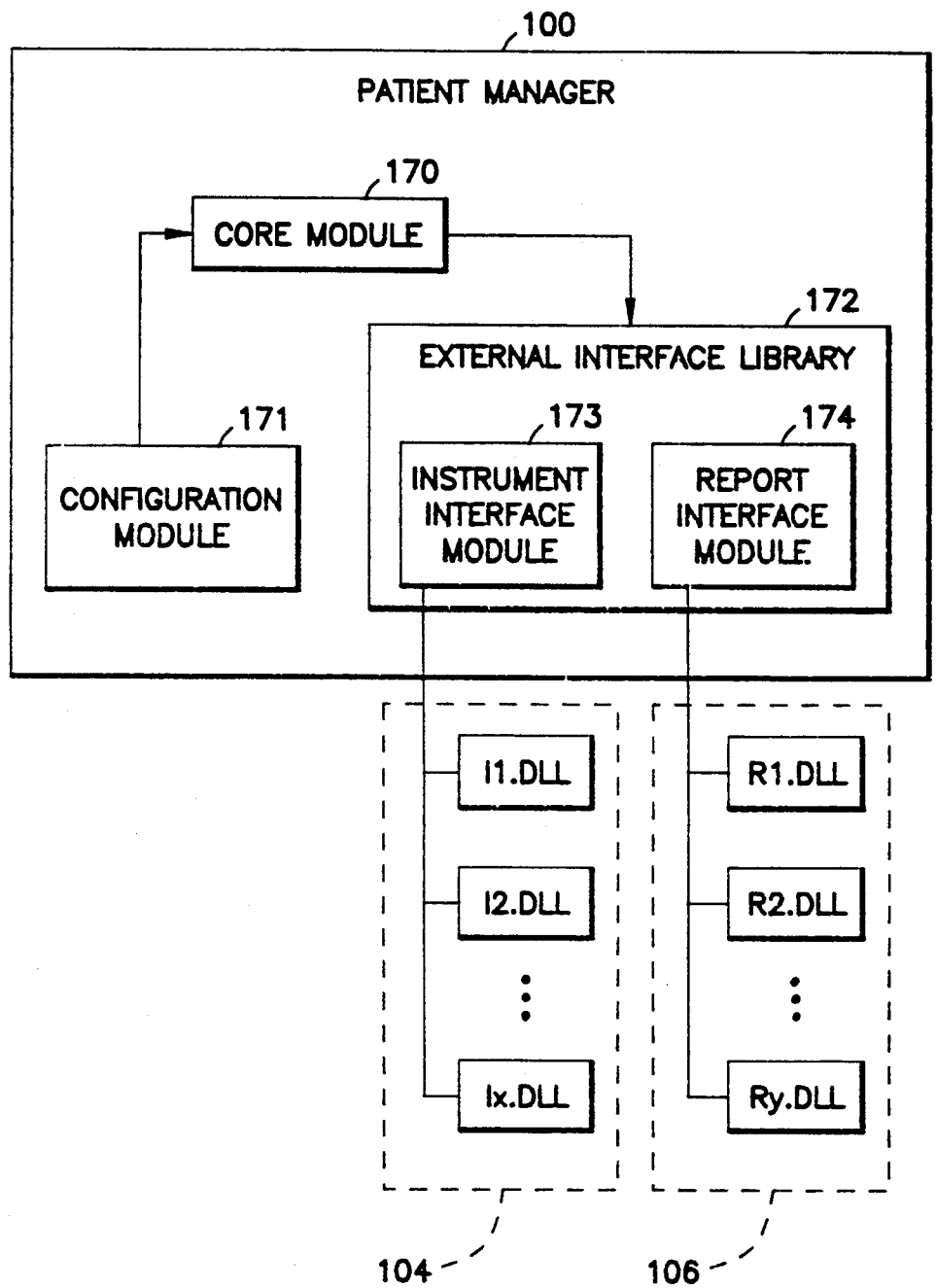
FIG. 1B is a block diagram showing the interface in the preferred system between the Patient Manager Module and the Instrument and Report Executables.

FIG. 1B is a more detailed block diagram showing a preferred interface between the Patient Manager 100 and the instrument and report executables. When the Patient Manager 100 initiate's a start up routine, the Core Module 170 of the Patient Manager accesses a Configuration Module 171. The Core Module 170 of the Patient Manager controls the Patient Manager and performs various management and organizational functions which will be explained below. The Core Module 170 examines configuration tables within the Configuration Module 171 to determine which instrument and report executables are available. For example, configuration tables may be defined as shown in Table 1.

TABLE 1

| CONFIGURATION TABLES | |
|---|---|
| TABLE IDENTIFIER | TABLE CONTENTS |
| Instlist | List of the available instrument executables I1.DLL - Ix.DLL |
| Rptlist | List of the available report executables R1.DLL - Ry.DLL |

The configuration tables in the Configuration Module 171 act as a list of pointers to the executables in the preferred system. The Patient Manager consults these lists to determine which functions are available in the executables of the preferred system. These functions are types of processing and reporting rules for managing and analyzing assessment information.

The instrument executables, for example, allow the preferred system to utilize assessment processing rules in order to perform administration of assessment information, such as objective test data or subjective client evaluations. The administration of assessment information by the instrument executables includes, but is not limited to, one or more of the following functions: (1) entering the assessment information into the preferred system; and (2) generating an assessment record to store the assessment information.

The report executables allow the preferred system to utilize the assessment reporting rules in order to perform reporting of the assessment information contained within the preferred system. The reporting of data by the report executables includes, but is not limited to, one or more of the following functions: (1) obtaining processed assessment information from the instrument executables; (2) interpreting the assessment information based upon the logic of the measurement tool used to obtain the assessment information; (3) scoring the assessment information, which may include, for example, normalizing and scaling the data of the assessment information; and (4) actually generating an assessment report.

Function (2), interpreting the assessment information, is based upon a particular logic for each measurement tool. Each standardized test, for example, will have its own logic for determining the meaning of the test results. For example, the MMPI, which contains all true-false questions, has logic which indicates which questions apply to particular personality aspects and how particular combinations of answers provides a distinct personality profile for the patient taking the test. The preferred system has the unique advantage of being able to adapt to the logic of multiple measurement tools and interpret assessment information from those measurement tools.

For each of the instrument executables 104 and report executables 106 on the system platform, a specific Dynamic Link Library ("DLL") is identified which implements the function of the instrument and report executables. The DLL's are function libraries that contain sets of functions which may be called by another executable. The DLL's are thus another form of executable and may be dynamically loaded and unloaded to perform the function identified by a particular DLL. For example, the Patient Manager executable may call a function from the instrument DLL to perform a particular operation explained below. The DLL's contain one set of functions for the instrument executables 104 (instrument DLL) and another set of functions for the report executables 106 (report DLL). Also, the DLL's may call other DLL's to perform a particular function, and DLL's may contain functions for both the instrument executables and report executables.

When the Core Module 170 of the Patient Manager 100 needs to access a function in the instrument or report DLL, the Core Module accesses the appropriate module in the External Interface Library 172. For an instrument DLL, the Core Module accesses the Instrument Interface Module 173, and for a report DLL, the Core Module accesses the Report Interface Module 174. The Instrument and Report Interface Modules perform the task of searching and accessing the appropriate DLL for the instrument or report executable of interest.

The executables, therefore, provide for a flexible system which can adapt to various forms of information and perform the same functions on different, or even incompatible, data or information. Each executable may perform a basic system function and be adapted to operate on a certain type of information such as a particular client test.

In summary, the preferred system platform 150 may access, via the Instrument Interface Module 173, first and second sets of assessment processing rules I1.DLL and I2.DLL in the instrument executables 104 for the purpose of administrating assessment information. A Patient Manager Module 100 (explained below) in the preferred system may input client identification information and may further organize both the client identification information and assessment information into lists of records. The Patient Manager Module in the preferred system may also link or associate records containing assessment information with records containing client identification information. Finally, the preferred system platform 150 may access, via the Report Interface Module 174, first and second sets of assessment reporting rules R1.DLL and R2.DLL in the report executables 106 for the purpose of generating a report of the assessments contained within the preferred system.

B. Patient Manager Module

The Patient Manager 100 maintains a list of patient records, typically one record for each patient. The Patient Manager performs the primary functions of organizing and managing patient information, including assessment information. For example, the Patient Manager may perform the function of recognizing which measurement tool was used to obtain the assessment information. The other two preferred modules perform secondary functions which will be explained below.

Figure 2:
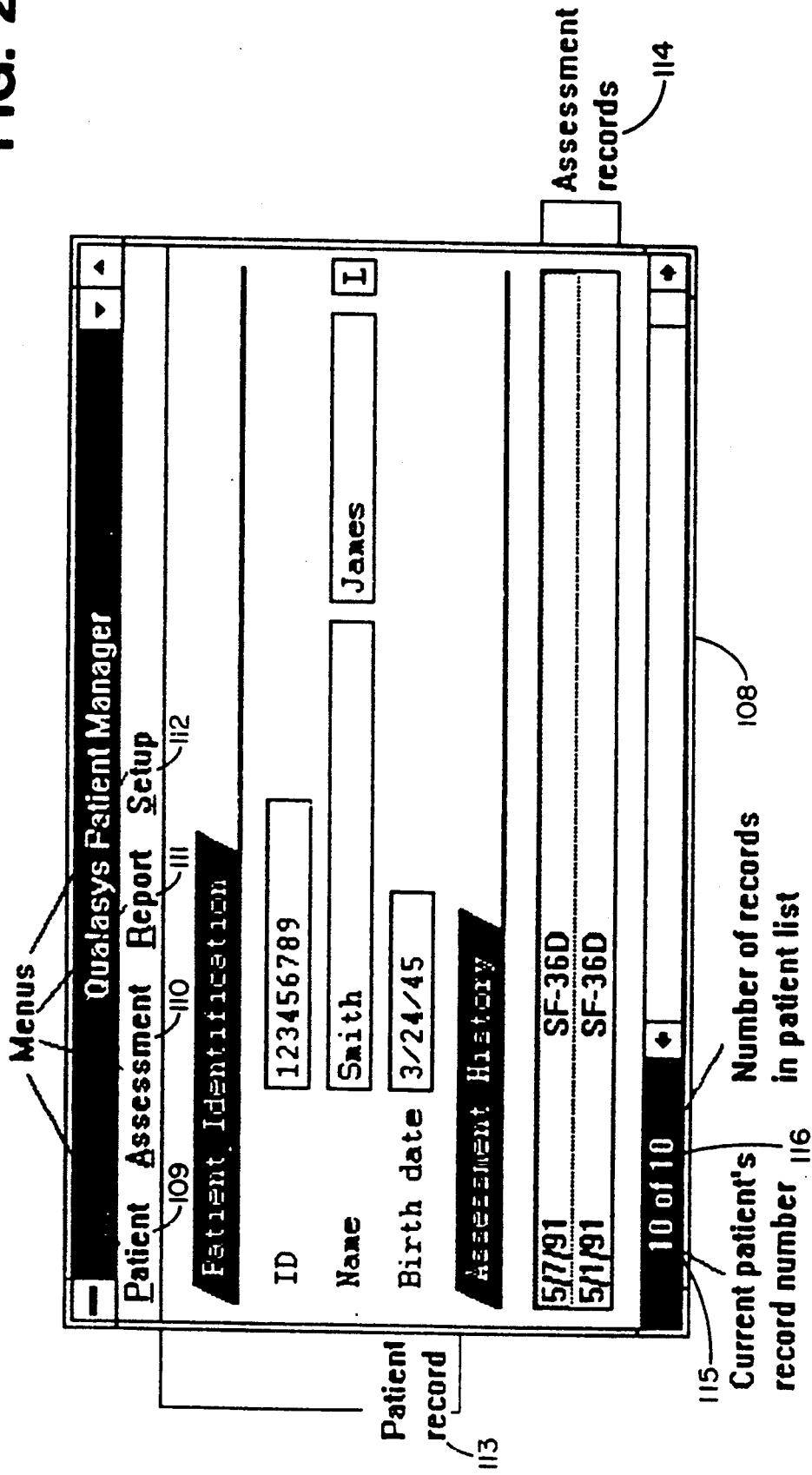
FIG. 2 represents a preferred user interface for accessing various parts of a Patient Manager Module.

The Patient Manager 100 operates on a series of patient records 113, which are shown represented by window 108 in FIG. 2. The Patient Manager may perform various functions, which are accessed via menus 109–112, on the patient records. The patient records may be a sequential list of database records. The fields of each patient record may be defined as shown in Table 2.

TABLE 2

| FIELD | MEANING |
|---|---|
| ID | Identification number for the patient. |
| Name | Name of the patient. |
| Birth date | Birth date of the patient. |
| Assessment History | List of zero or more assessment records, identified by date and test, for the current patient. |
| RecordID | Sequential number identifying this record. |

The RecordID field may be represented in window 108 by field 115, which displays the number of the current patient record. For example, as shown in FIG. 2, there are ten records in the patient list as shown by field 116, and the patient record shown as window 108 is the tenth record in the list.

The Assessment History field contains a list of zero or more assessment records 114 for the current patient record. Each assessment record is identified by the date of the assessment and the type of assessment.

1. Patient Manager/Database Server Interface

Many of the functions performed by Patient Manager 100, as shown by the flow charts, are performed with the assistance of Database Server 101. FIG. 1C shows the interface in the preferred system between the Patient Manager and the Database Server. The Patient Manager and Database Server communicate through Message File 175 in a type of handshaking process.

Figure 1E:
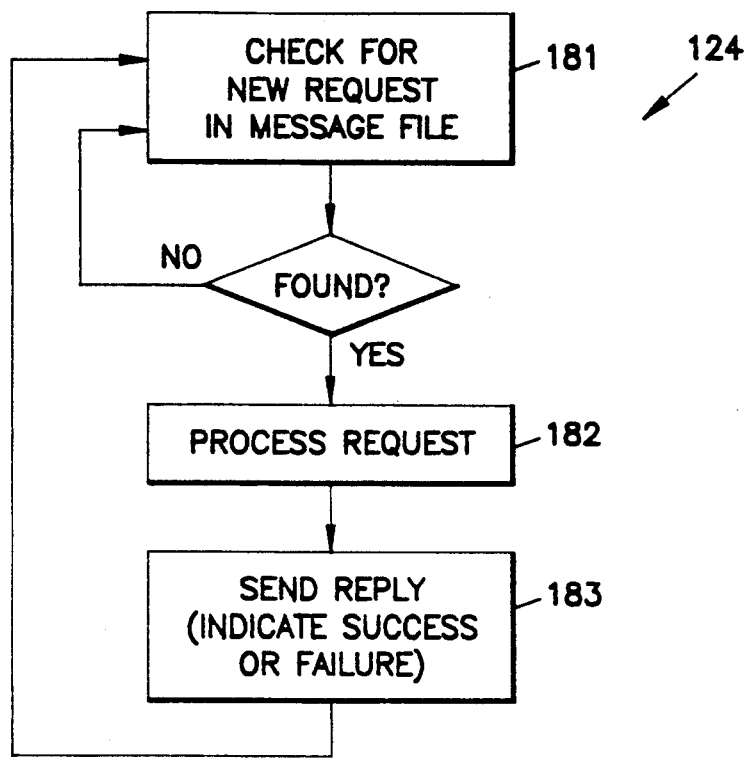
FIG. 1E shows a preferred flow of data executed by the Database Server Module for retrieving and processing a request from the Message File.
Figure 1C:
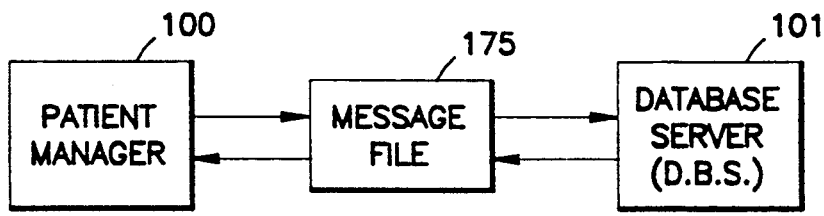
FIG. 1C is a block diagram showing the interface in the preferred system between the Patient Manager Module and Database Server Module.
Figure 1D:
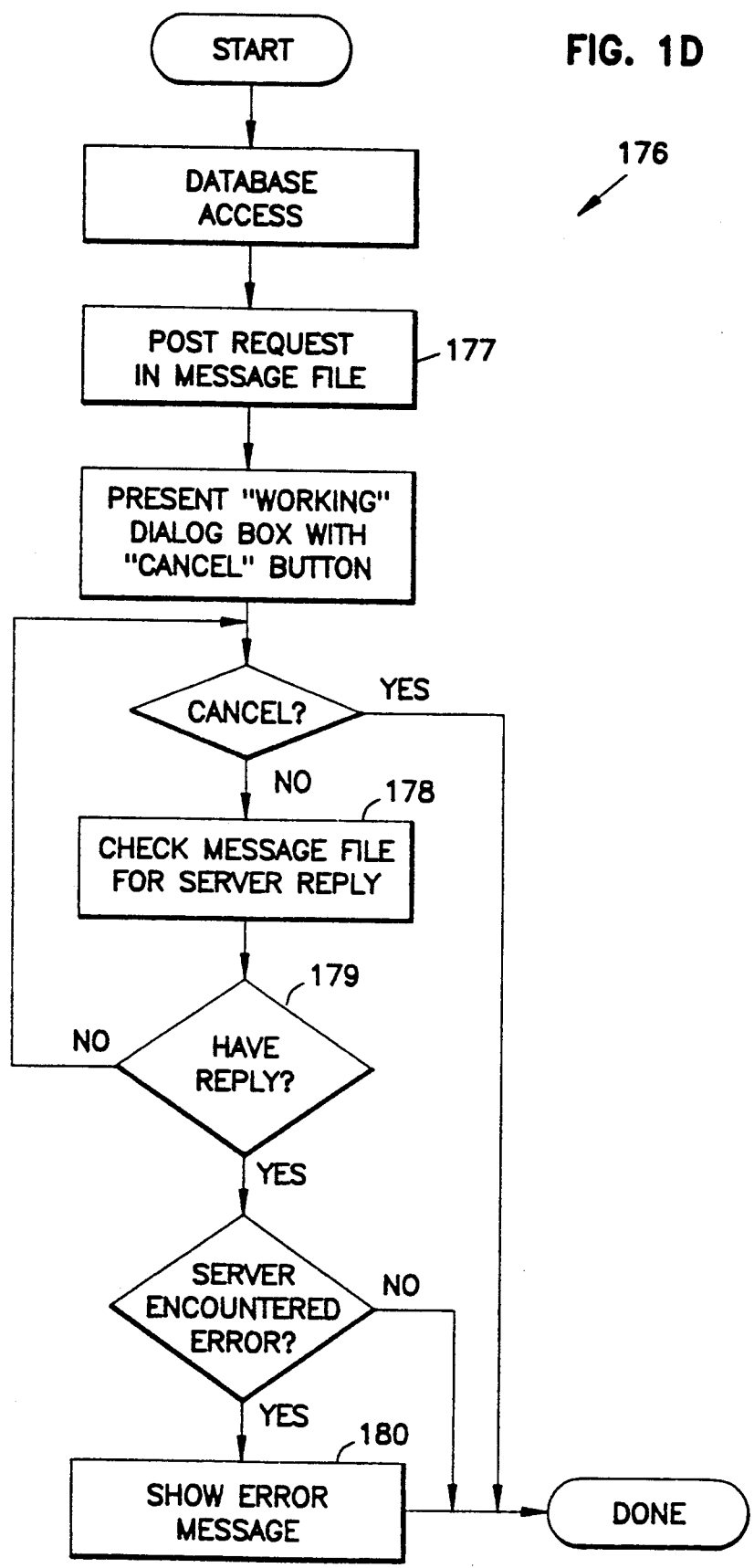
FIG. 1D shows a preferred flow of data executed by the Patient Manager Module for sending a request to the Database Server Module via the Message File.

FIG. 1D shows the preferred flow of data executed by the Patient Manager for the purpose of sending a request to the Database Server. The request sent to the Database Server may include, for example, various database operations as explained below. The Patient Manager first posts a request for an operation in Message File 175 at step 177. At steps 178–179, the Patient Manager waits for the Database Server to acknowledge receipt of the request. The Database Server sends a reply, which will contain either a success or an error message (step 180), in response to the request of the Patient Manager.

FIG. 1E shows the preferred flow of data executed by the Database Server for the purpose of retrieving and processing a request from Message File 175. The Database Server continually monitors Message File 175 at step 181 for new requests from the Patient Manager. When a request is found, the Database Server processes the request at step 182. Upon completion of the processing, the Database Server sends a reply, at step 183, to the Patient Manager via the Message File.

2. Patient Records and Operations a. Add

Figure 3:
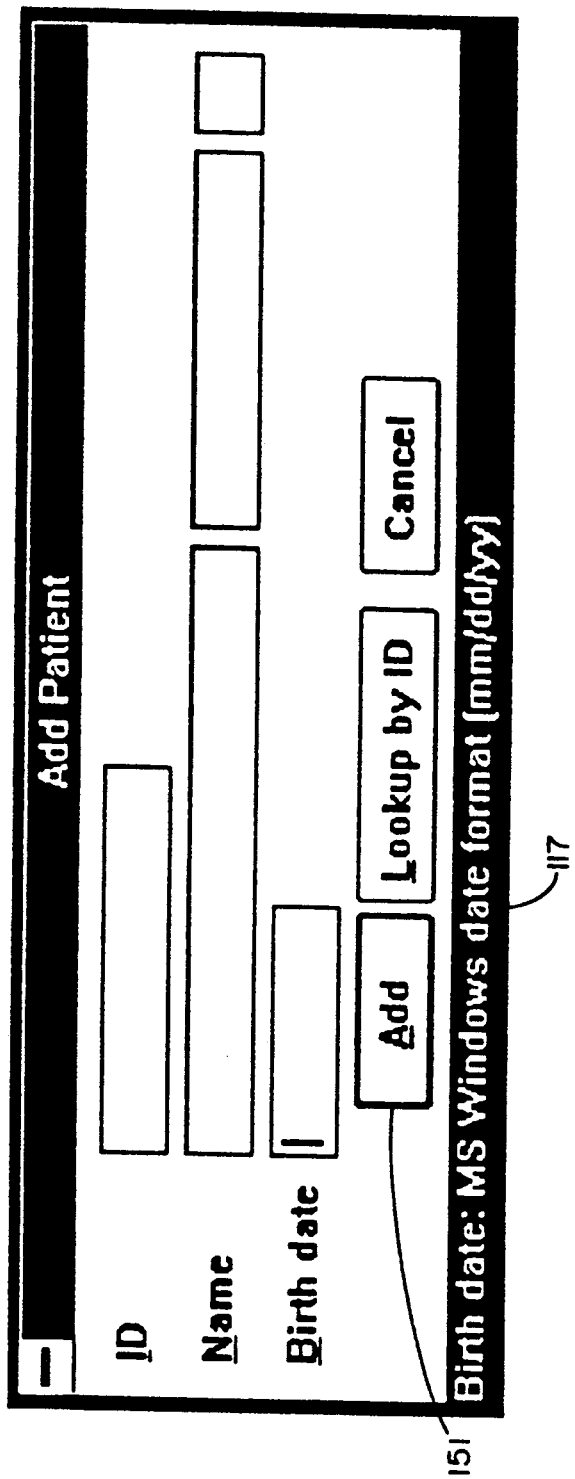
FIG. 3 represents a preferred user interface for adding a patient record.
Figure 4:
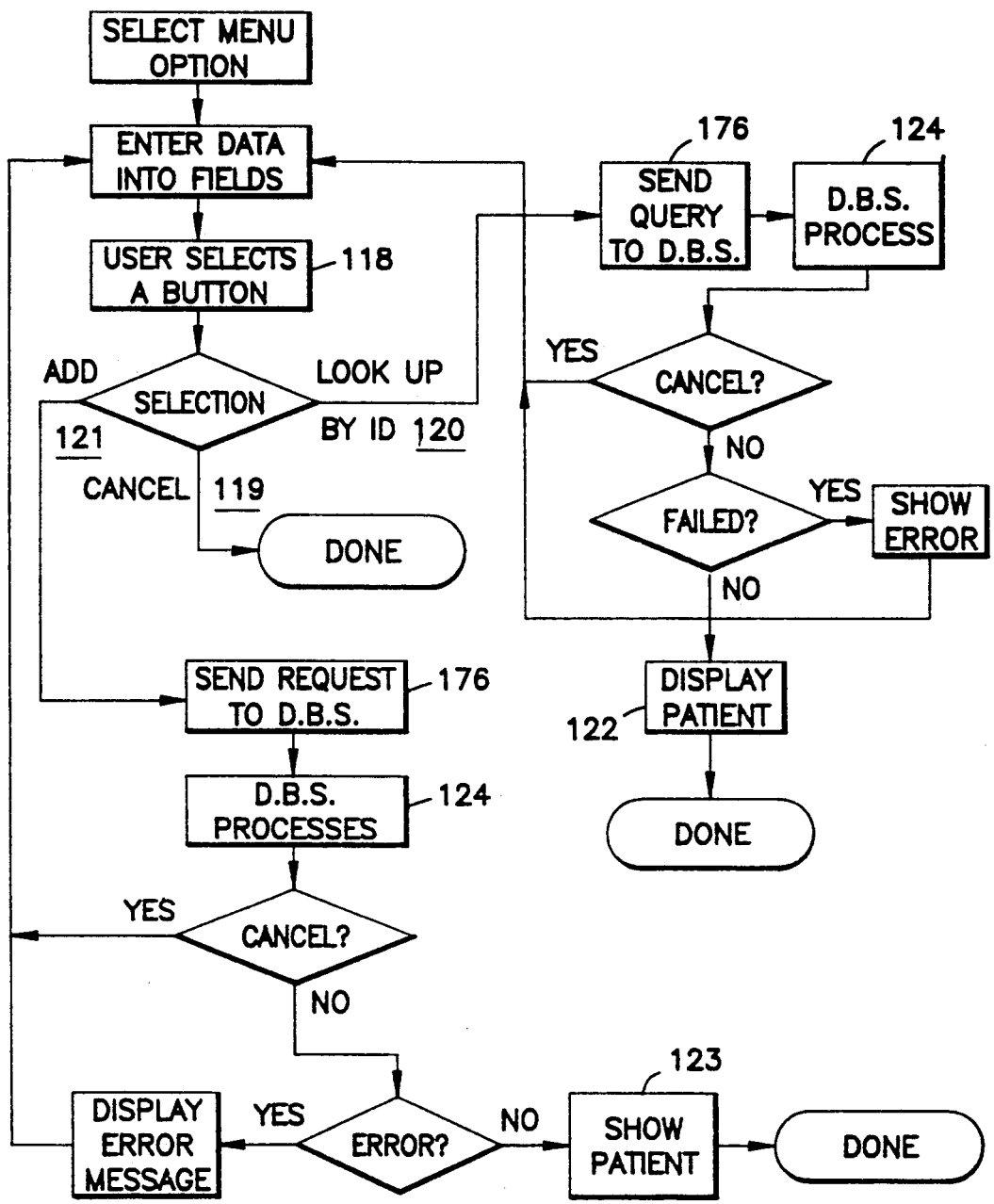
FIG. 4 represents a preferred flow of data through a process of adding a patient record.

The ADD operation allows a user to add a patient record to a preferred database for the system. FIG. 3 shows a preferred user interface for creating a new patient record. In the system as disclosed, this operation is accessed by the Patient Menu 109 in the Patient Manager Window 108. FIG. 4 shows the preferred flow of data through the ADD operation for the system. Within steps 118–121, the system, based on the user's selection, may cancel the operation at step 119, look up an identification ("ID") number in the database at step 120, or add the user-entered patient information to the database at step 121. The look up by ID step 120 may be performed so that the system may check the database for the user-entered ID number to determine if a patient record has already been created for this ID number. If a patient record was found for the entered ID number, the system displays that patient record at step 122.

When the user selects add button 151 in window 117, the system writes the user entered information to a preferred database at step 124. Throughout the drawings, "D.B.S." refers to the preferred Database Server Module and identifies a step that is performed by that module. For example, at step 124, the Database Server Module receives the user entered information from the Patient Manager Module via the Message File, and the Database Server creates a new record for this information. The system also creates a new patient list with only the added patient record. After the new patient record is created, the system displays the patient record at step 123.

b. Retrieve

Figure 5:
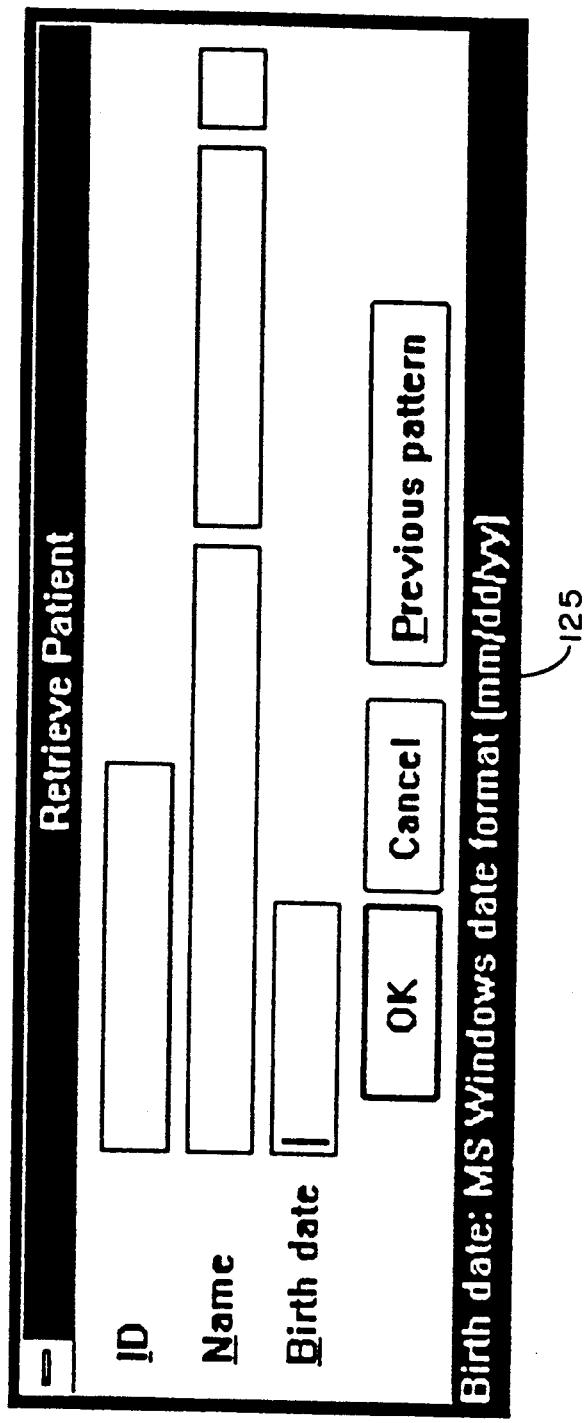
FIG. 5 represents a preferred user interface for retrieving a patient record.
Figure 6:
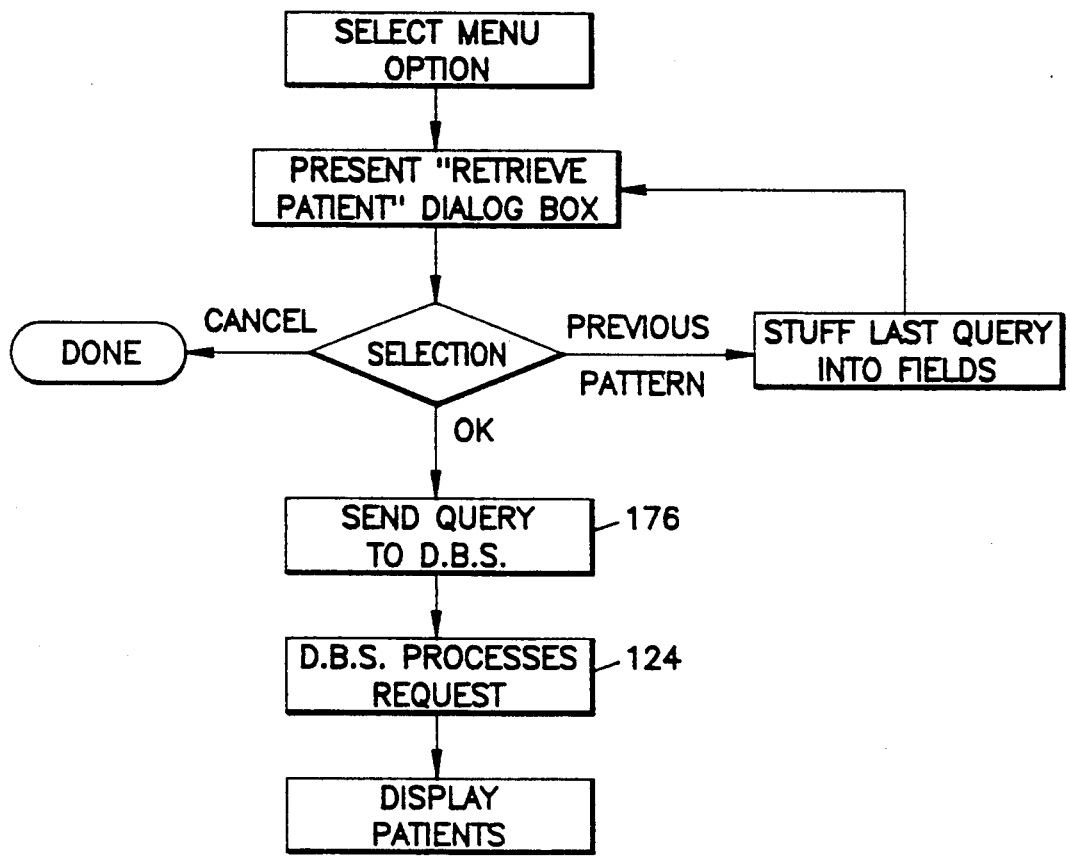
FIG. 6 represents a preferred flow of data through a process of retrieving a patient record.

The preferred RETRIEVE operation allows the system to search a database for one or more patient records. In the system as disclosed, the user accesses the RETRIEVE operation via Patient Menu 109 in Patient Manager Window 108. The system may be configured to present the user with a window 125 as shown in FIG. 5 for the purpose of initiating a RETRIEVE operation, the preferred flow of data of which is shown in FIG. 6.

The system may search through the patient records by the ID, Name, or Birth date fields, or a combination thereof. For example, the user may want to search for all patients with the same birth date. If a patient record was found during the search, the system displays that patient record. If more than one patient record was found, the system sorts the retrieved patient records alphabetically by name and displays the first patient record in the list of retrieved patient records.

c. Update

Figure 7:
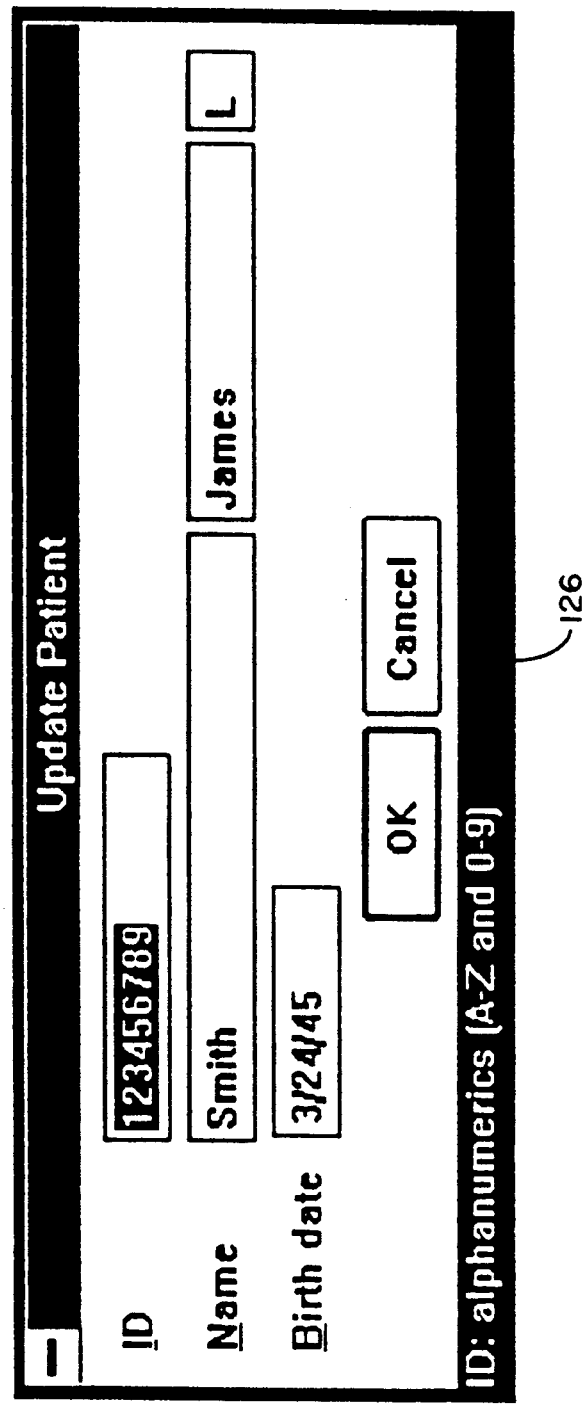
FIG. 7 represents a preferred user interface for updating a patient record.
Figure 8:
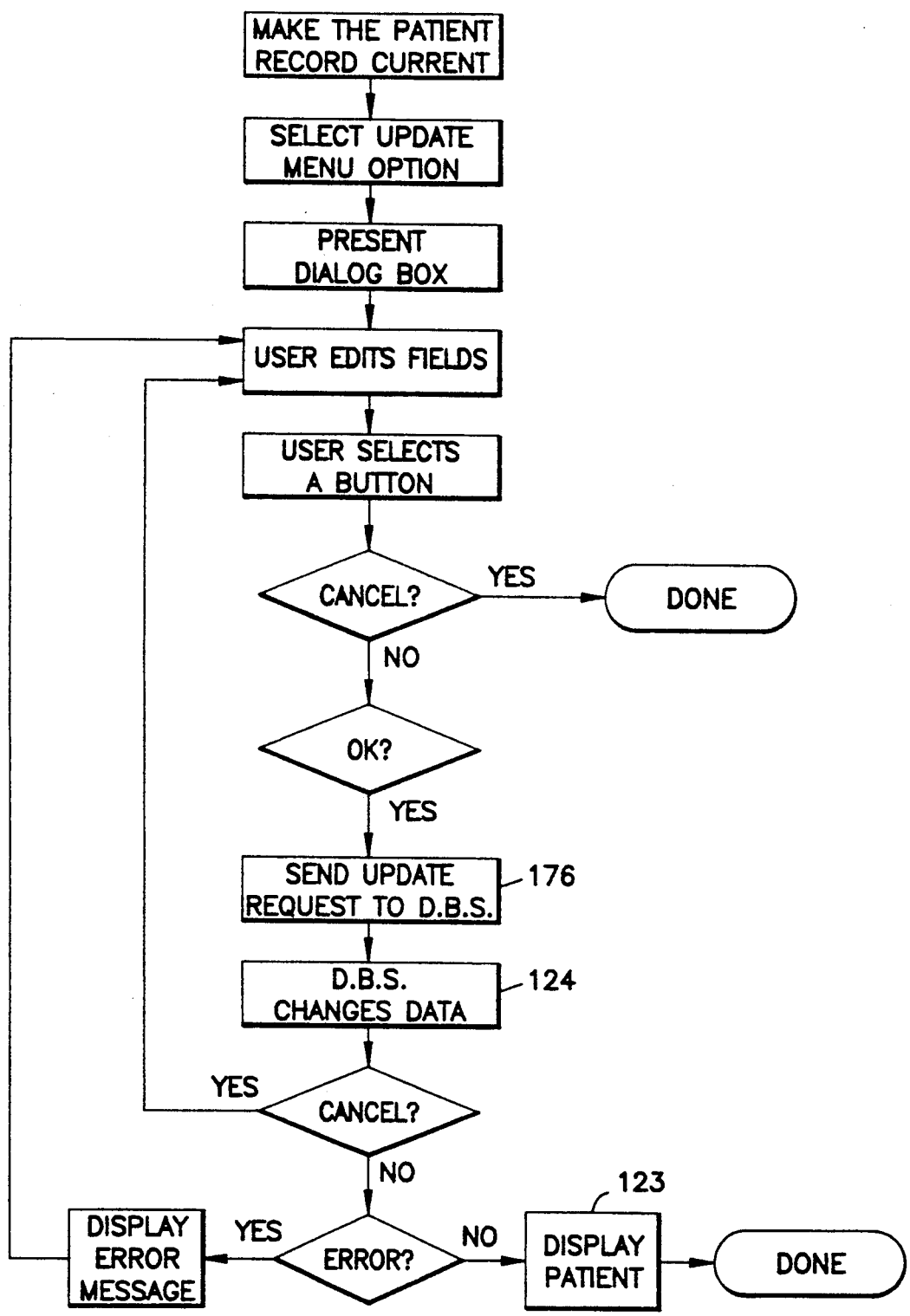
FIG. 8 represents a preferred flow of data through a process of updating a patient record.

The preferred UPDATE operation allows the system to change the information in the fields of an existing patient record which is being displayed in the Patient Manager window. In the system as disclosed, the user accesses the UPDATE operation via Patient Menu 109 in Patient Manager Window 108. The system may be configured to present the user with a window 126 as shown in FIG. 7 for the purpose of initiating an UP- DATE operation, the preferred flow of data of which is shown in FIG. 8. During the UPDATE operation, the system writes the user-entered information into the appropriate fields of the patient record which has already been located through a search.

d. Delete

Figure 9:
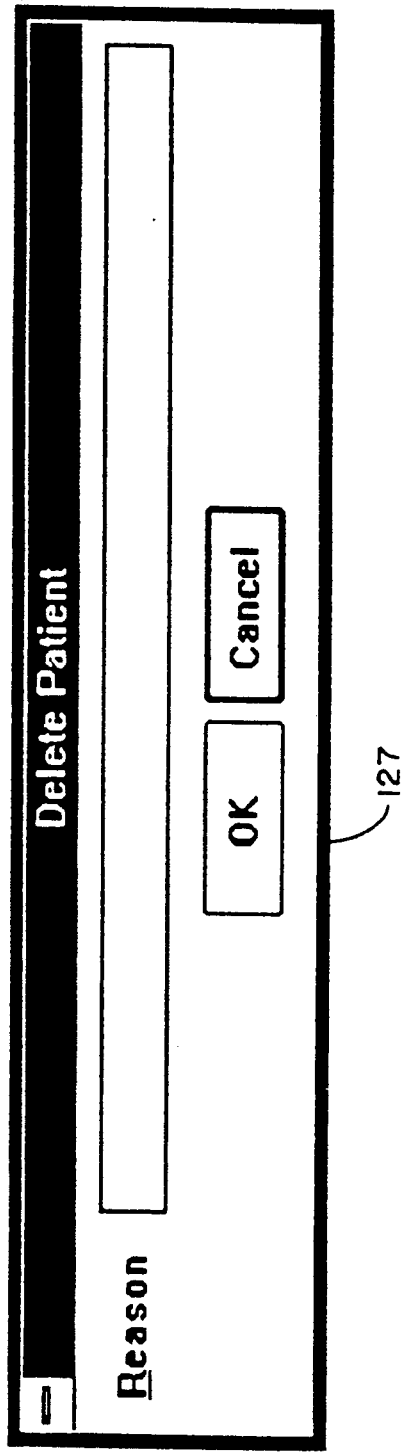
FIG. 9 represents a preferred user interface for deleting a patient record.
Figure 10:
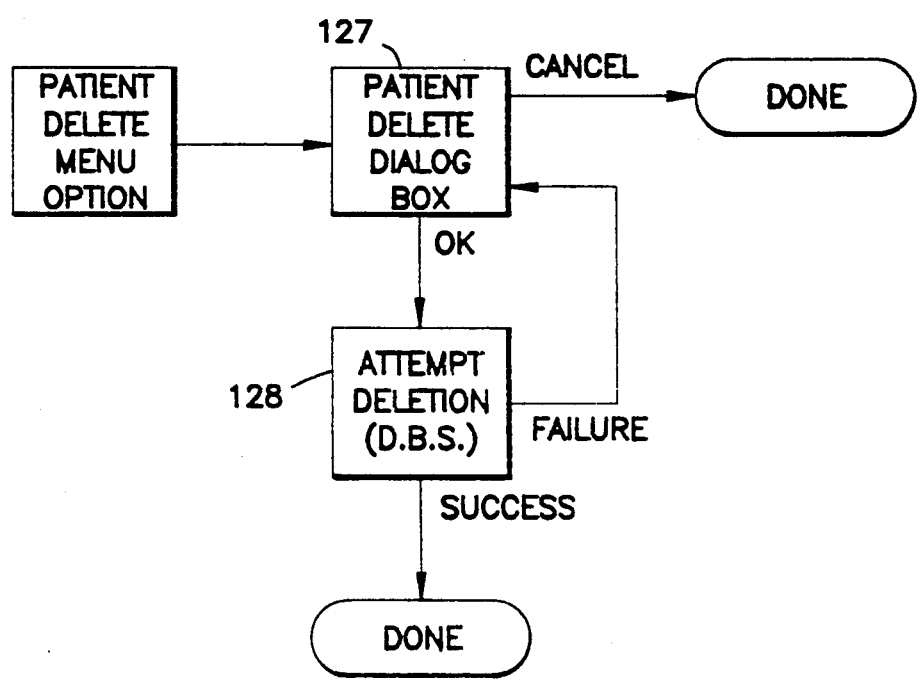
FIG. 10 represents a preferred flow of data through a process of deleting a patient record.

The preferred DELETE operation allows the system to remove a patient record from the database. In the system as disclosed, the user accesses the DELETE operation via Patient Menu 109 in Patient Manager Window 108. The system may be configured to present the user with a window 127 as shown in FIG. 9 for the purpose of initiating a DELETE operation, the preferred flow of data of which is shown in FIG. 10. The user may enter a reason for deletion as shown in window 127. The system attempts deletion of a patient record in step 128 by deleting the record and creating a new list of patient records not including the deleted patient record.

3. Assessment Records and Operations

The preferred system maintains a series of assessment records that are linked to the corresponding patient records (see the Assessment History Field in FIG. 2). The assessment records maintain the actual objective and subjective data which characterizes a patient's progress and is thus useful in measuring the effectiveness of the patient's treatment. The system typically maintains one assessment record for each occurrence of an assessment. For example, the system may have one assessment record for each time that a patient took a particular test. Each assessment record would then contain the raw test results for a particular occurrence of the test. The fields of the assessment records will depend upon the parameters of each type of test. Each type of test may have varying types and numbers of questions or queries. The system will typically have assessment records tailored to meet the needs of each type of test. Each type of assessment record will preferably have a field for each test entry or user answer. The assessment records may also have a text field where a therapist may enter subjective information regarding a patient's progress and response to treatment.

The Patient Manager Module has various functions available under the Assessment Menu 110 in Patient Manager Window 108 for operating on the assessment records.

a. Scan

Figure 11:
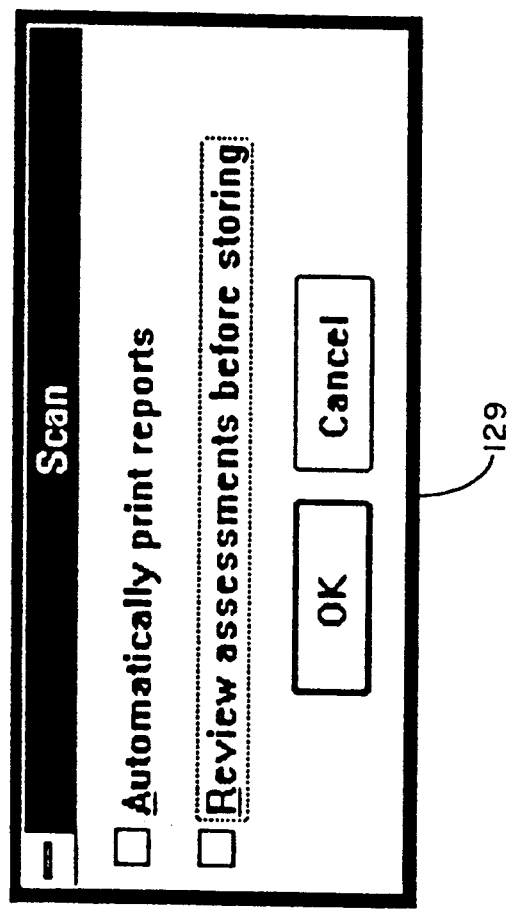
FIG. 11 represents a preferred user interface for initiation of a scanning process which allows review and automatic printing of reports.
Figure 14:
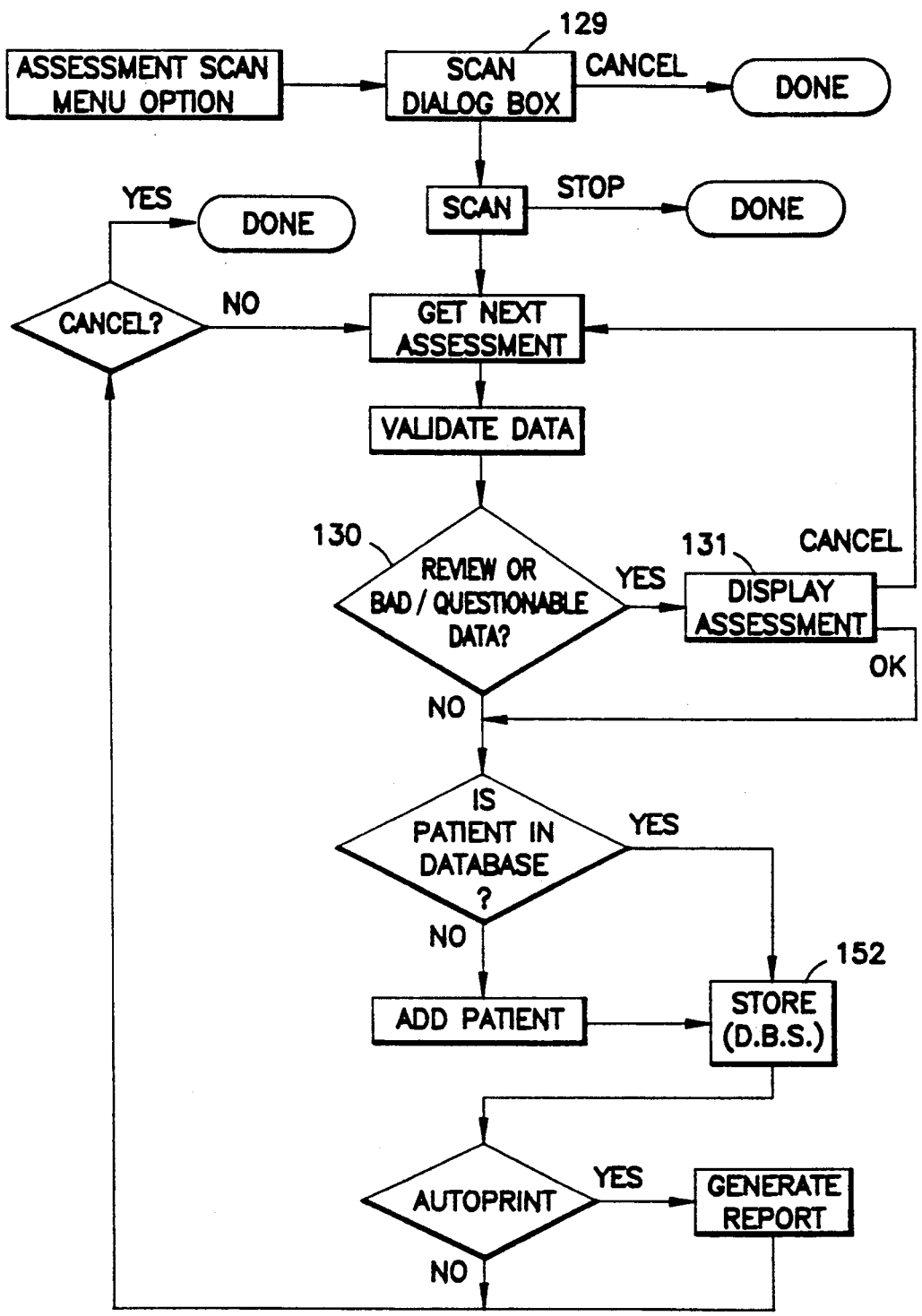
FIG. 14 represents a preferred flow of data through a process of scanning an assessment.

The preferred SCAN operation allows the system to create assessment records by scanning the hard copies of raw test data. In the system as disclosed, the user accesses the SCAN operation via Assessment Menu 110 in Patient Manager Window 108. The system may be configured to present the user with a window 129 as shown in FIG. 11 for the purpose of initiating a SCAN operation, the preferred flow of data of which is shown in FIG. 14. The preferred system provides users the options of automatically printing (after storing) and reviewing (before storing) the scanned assessment information before the assessment information is written to a new assessment record in the database.

Figure 12:
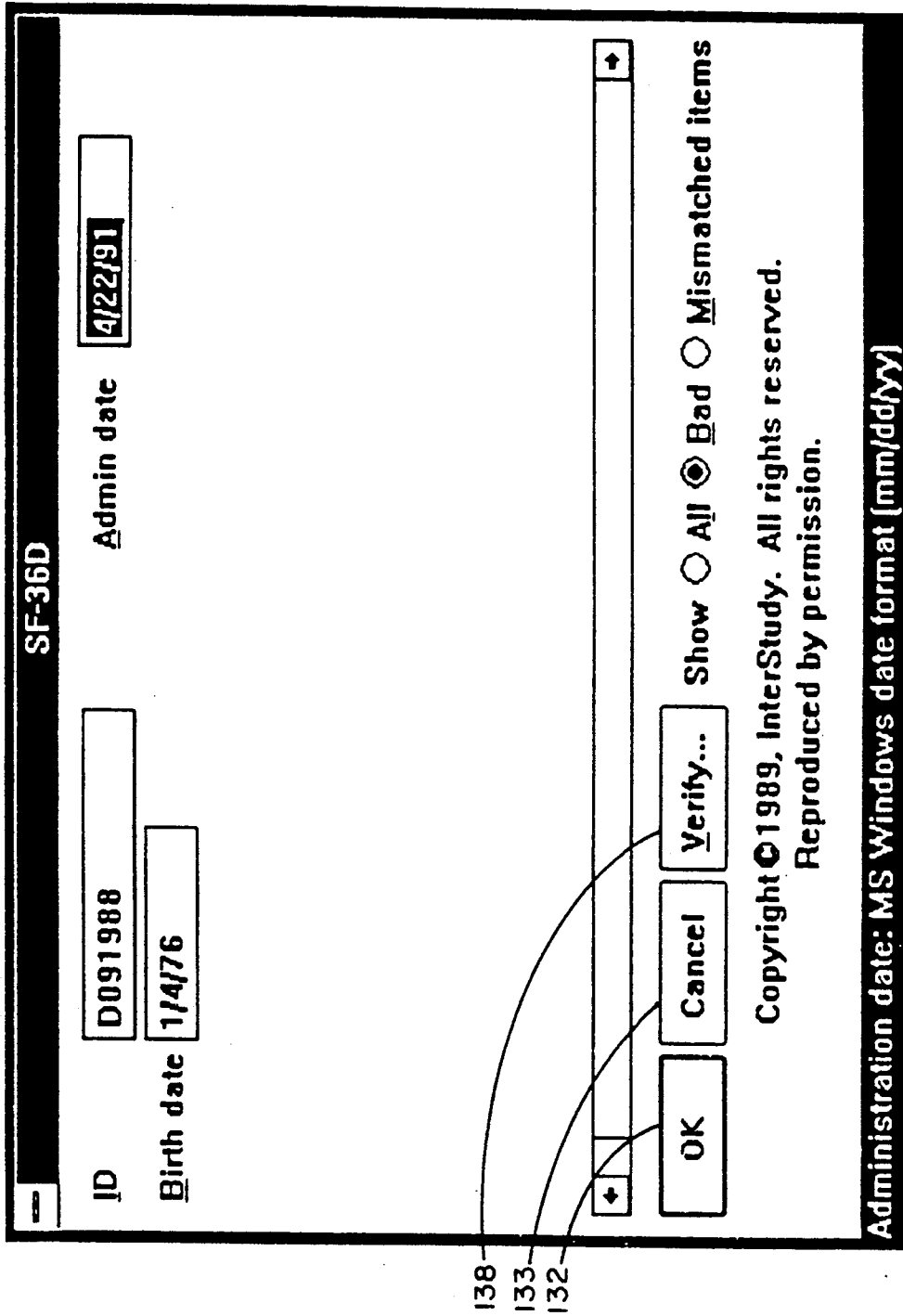
FIG. 12 represents a preferred user interface for reviewing assessments while scanning and before storing.
Figure 13:
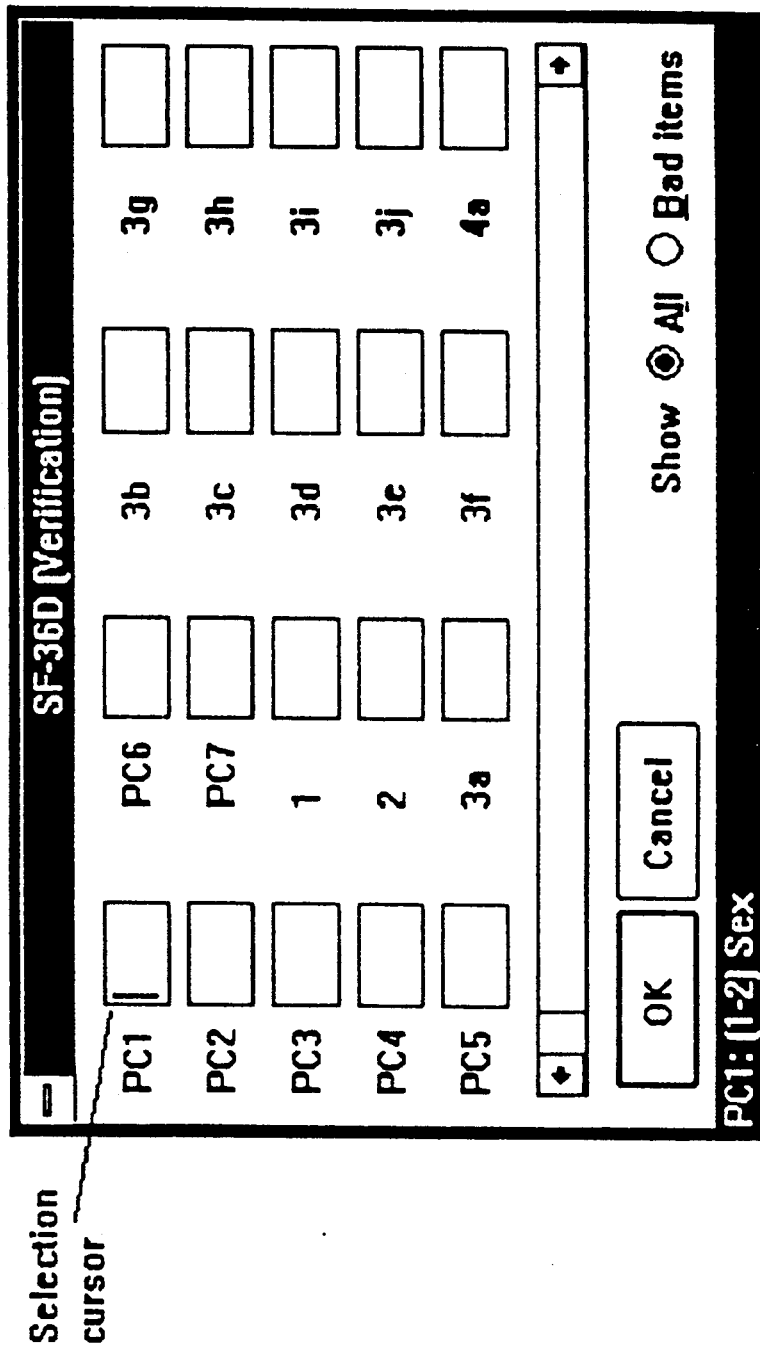
FIG. 13 represents a preferred user interface for reentering assessment data for verification.

As shown in FIG. 13, if the user elects to review the assessments, the system branches into a review function at step 130 (see FIG. 14). At step 131, the system displays the scanned data. An example of a user interface for reviewing scanned test data is shown as window 137 in FIG. 12. If the user selects verify button 138, the system presents a verification window such as window 134 as shown in FIG. 13. The verification window 134 allows the user to manually reenter test data and compare the entered test data with any data previously entered for the same occurrence of this assessment.

If the user selects cancel button 133 in window 137, the system does not create an assessment record for the current assessment and instead scans the next assessment. If the user selects OK button 132 (window 137) in the verification operation, the system creates a new assessment record in the database for the current assessment at step 152.

b. Manual Entry

Figure 15:
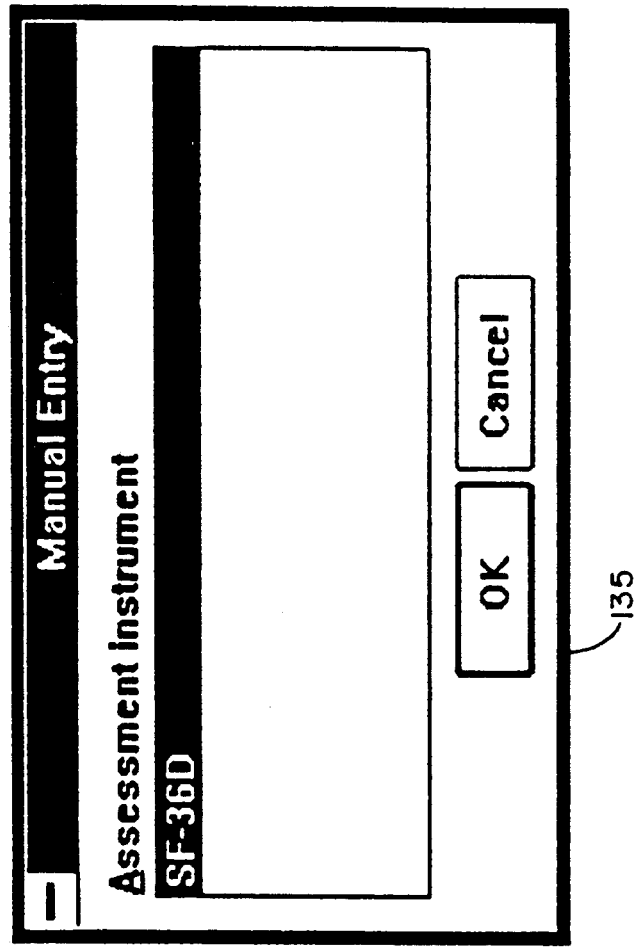
FIG. 15 represents a preferred user interface for selecting an instrument for manual entry of assessments.
Figure 16:
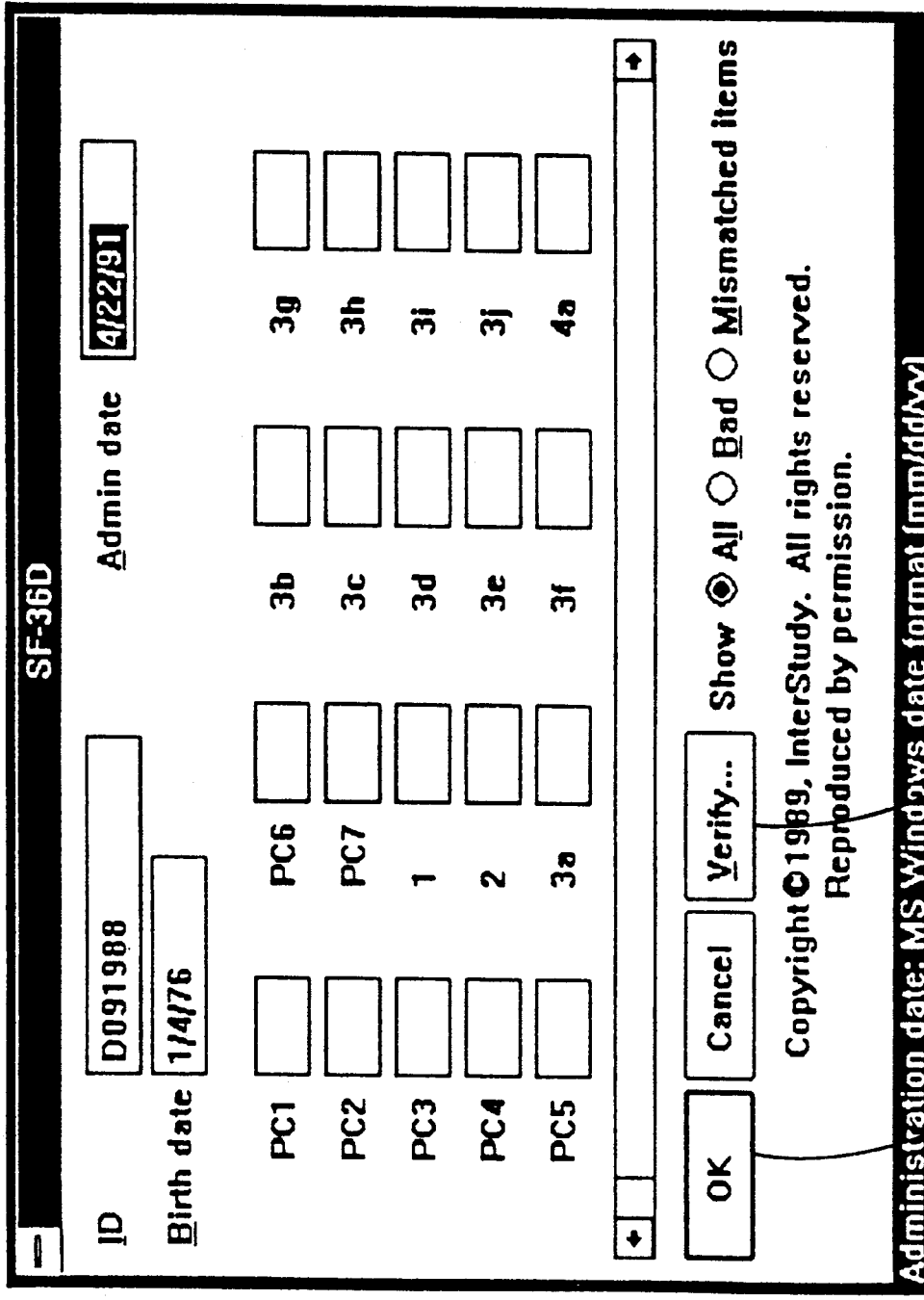
FIG. 16 represents a preferred user interface for manually entering and verifying assessments.
Figure 17:
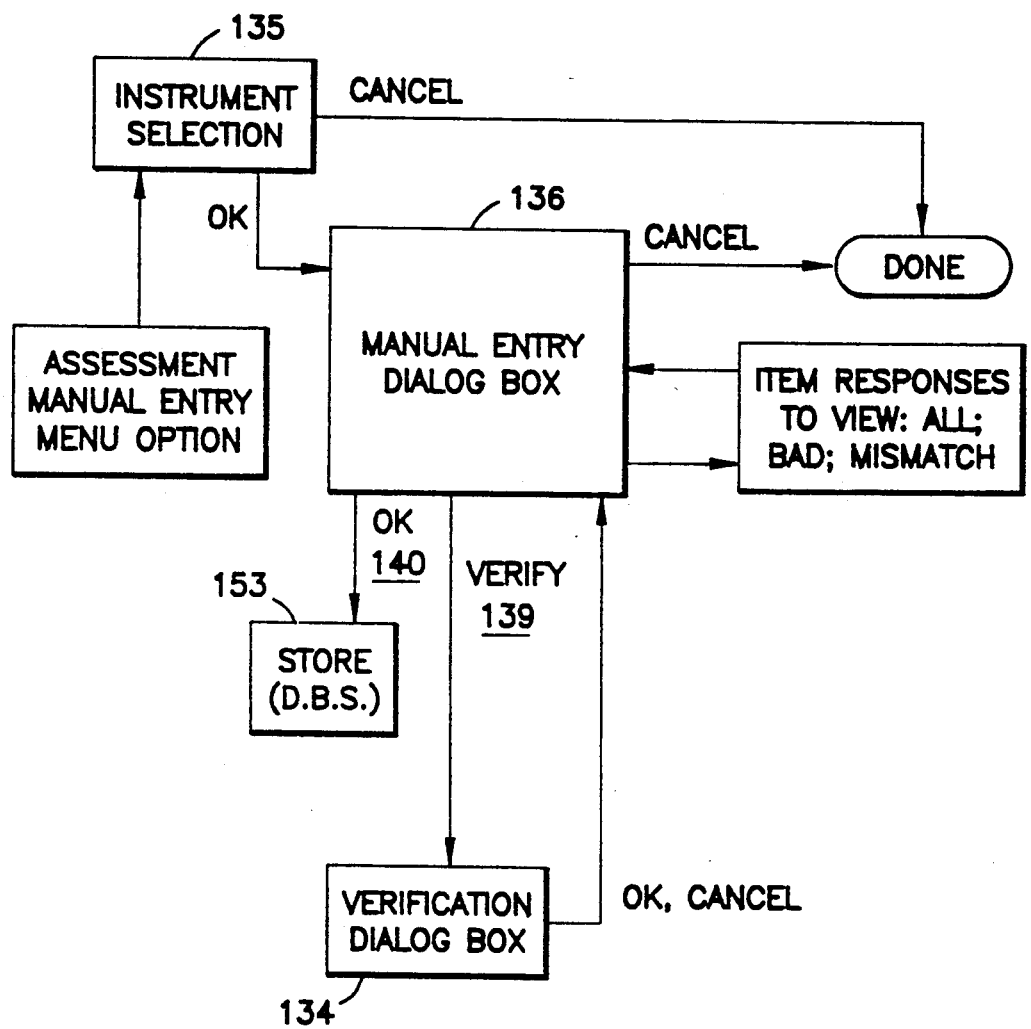
FIG. 17 represents a preferred flow of data through a process of manually entering an assessment.

The preferred MANUAL ENTRY operation allows the system to create assessment records from data manually entered by a user. In the system as disclosed, the user accesses the MANUAL ENTRY operation via Assessment Menu 110 in Patient Manager Window 108. The system may be configured to present the user with a window 135 as shown in FIG. 15 for the purpose of initiating a MANUAL ENTRY operation, the preferred flow of data of which is shown in FIG. 17. After a user has selected an assessment instrument in window 135, which may be a particular type of test, a preferred system presents the user with a window for entering the assessment information. An example of a window for entering assessment information for the SF-36D test is window 136 as shown in FIG. 16. If the user selects verify button 139 in window 136, the preferred system presents a verification window such as window 134 as shown in FIG. 13. As with the scanning of assessments, the preferred system allows the user to compare the entered assessment information with previously entered information for the same assessment occurrence. After the user has entered assessment information, the user may select OK button 140 in window 136 to store the information. When the user selects button 140, a preferred system writes the user entered assessment information to a new assessment record in the database at step 153.

c. Move

Figure 18:
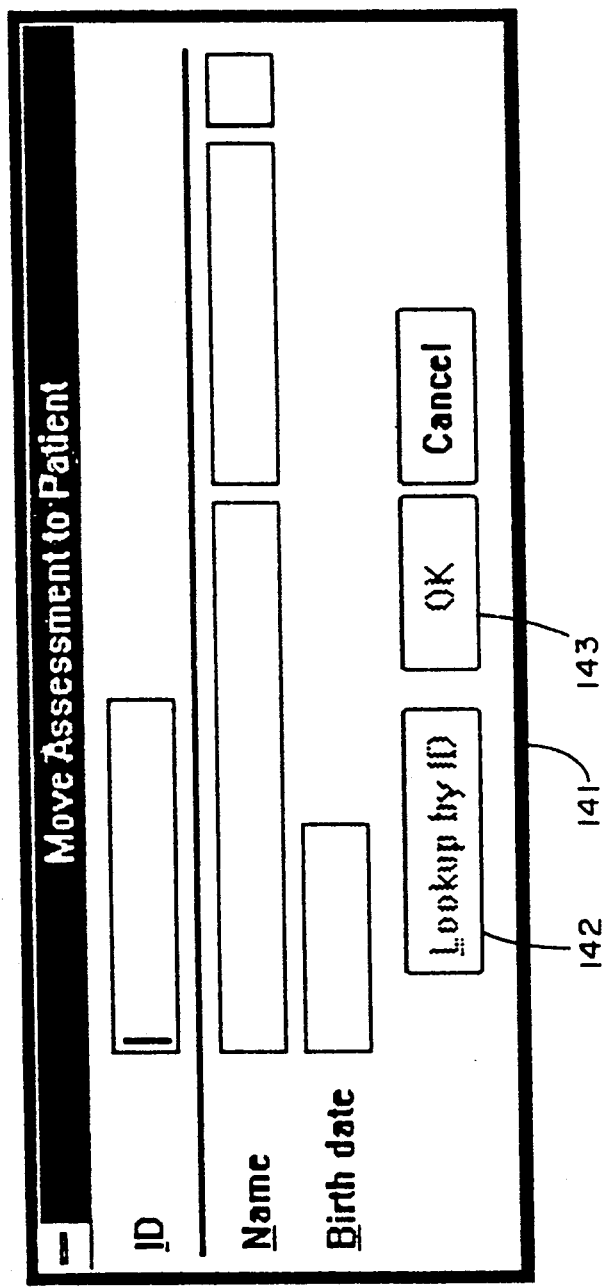
FIG. 18 represents a preferred user interface for moving an assessment to a patient record.
Figure 19:
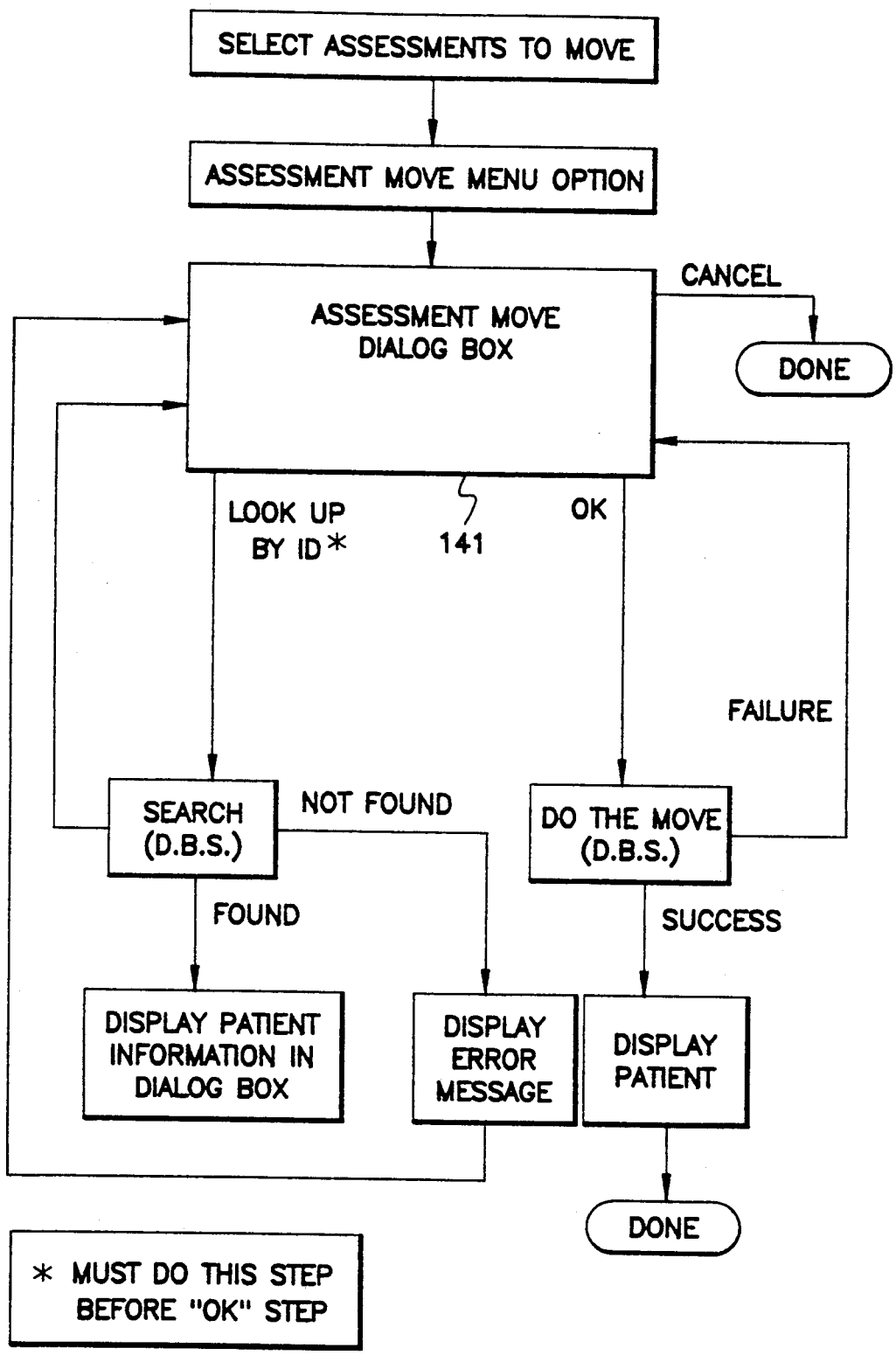
FIG. 19 represents a preferred flow of data through a process of moving an assessment record.

The preferred MOVE operation allows the system to remove an assessment record from one patient record and attach it to another patient record. In the system as disclosed, the user accesses the MOVE operation via Assessment Menu 110 in Patient Manager Window 108. The system may be configured to present the user with a window 141 as shown in FIG. 18 for the purpose of initiating a MOVE operation, the preferred flow of data of which is shown in FIG. 19. Before selecting a menu option, the user selects one or more assessment records and then enters the ID number of the patient. The preferred system for the patient record with the entered ID number when the user selects the Look up by ID button 142. If the system locates the corresponding patient record, the system displays the information for this patient record. Next, when the user selects OK button 143, the preferred system links the selected assessment records with the located patient record and enters the assessment in the Assessment History Field of the target patient record.

d. Delete

Figure 20:
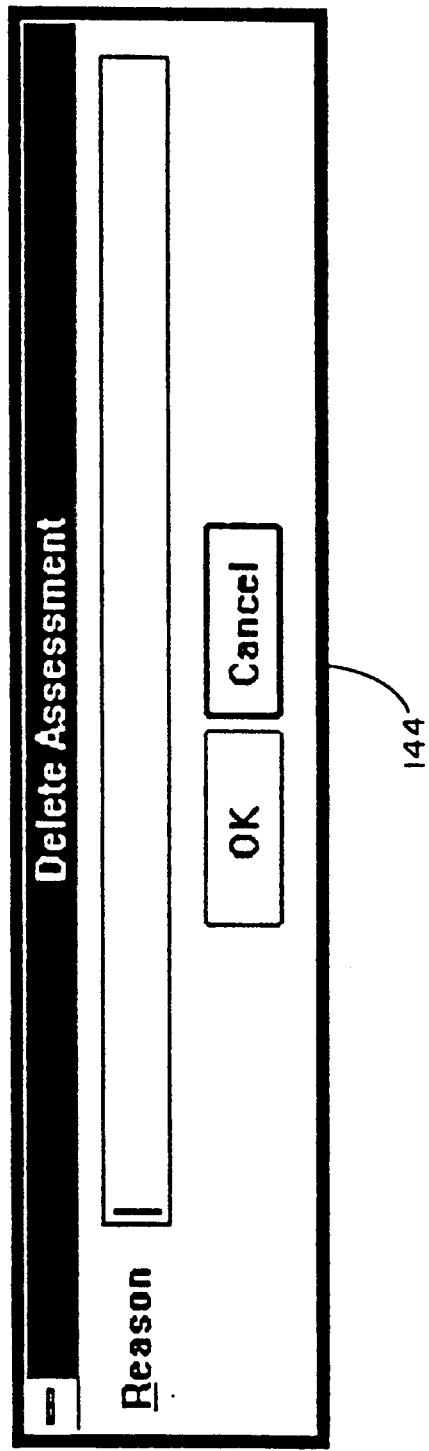
FIG. 20 represents a preferred user interface for deleting an assessment record.
Figure 21:
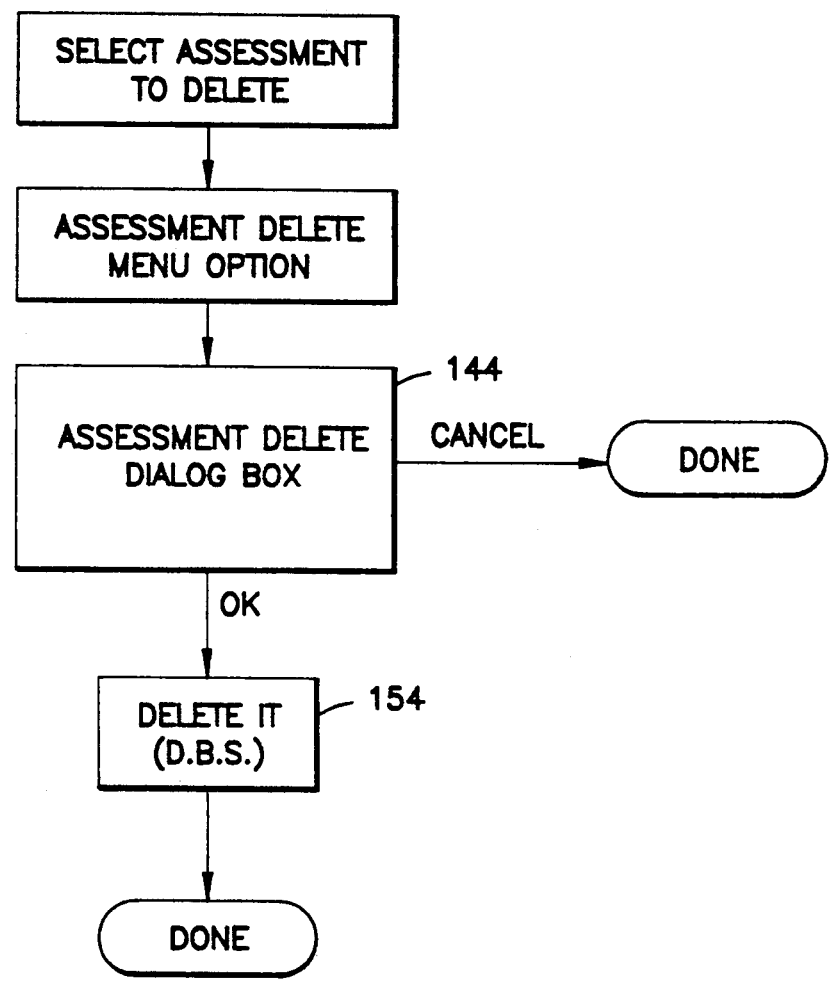
FIG. 21 represents a preferred flow of data through a process of deleting an assessment record.

The preferred DELETE operation allows the system to remove one or more assessment records from a database. In the system as disclosed, the user accesses the DELETE operation via Assessment Menu 110 in Patient Manager Window 108. The system may be configured to present the user with a window 144 as shown in FIG. 20 for the purpose of initiating a DELETE operation, the preferred flow of data of which is shown in FIG. 21. The preferred system allows the user to enter a reason for the deletion as shown in window 144. If the user elects to delete the one or more selected assessments, a preferred system removes it from the database at step 154.

4. Report Operations

Figure 22:
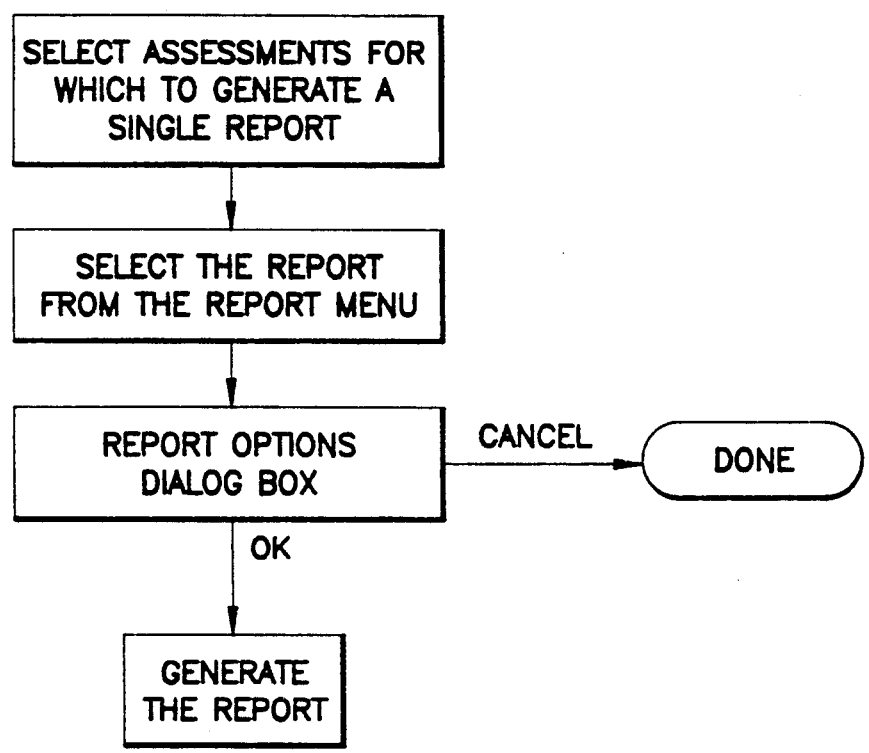
FIG. 22 represents a preferred flow of data through a process of generating a report for one or more assessment records.

Report Menu 111 in Patient Manager Window 108 allows the preferred system to list reports that can be generated for the selected assessment records in the Assessment History Field of the current patient record. The preferred flow of data for generating the reports is shown in FIG. 22. The type of reports available will depend upon the available assessments, since the each assessment may have different reporting requirements and capabilities due to varying types of data contained within the assessments. One report may combine data from multiple assessments with potentially different data.

5. Setup Operations

Figure 23:
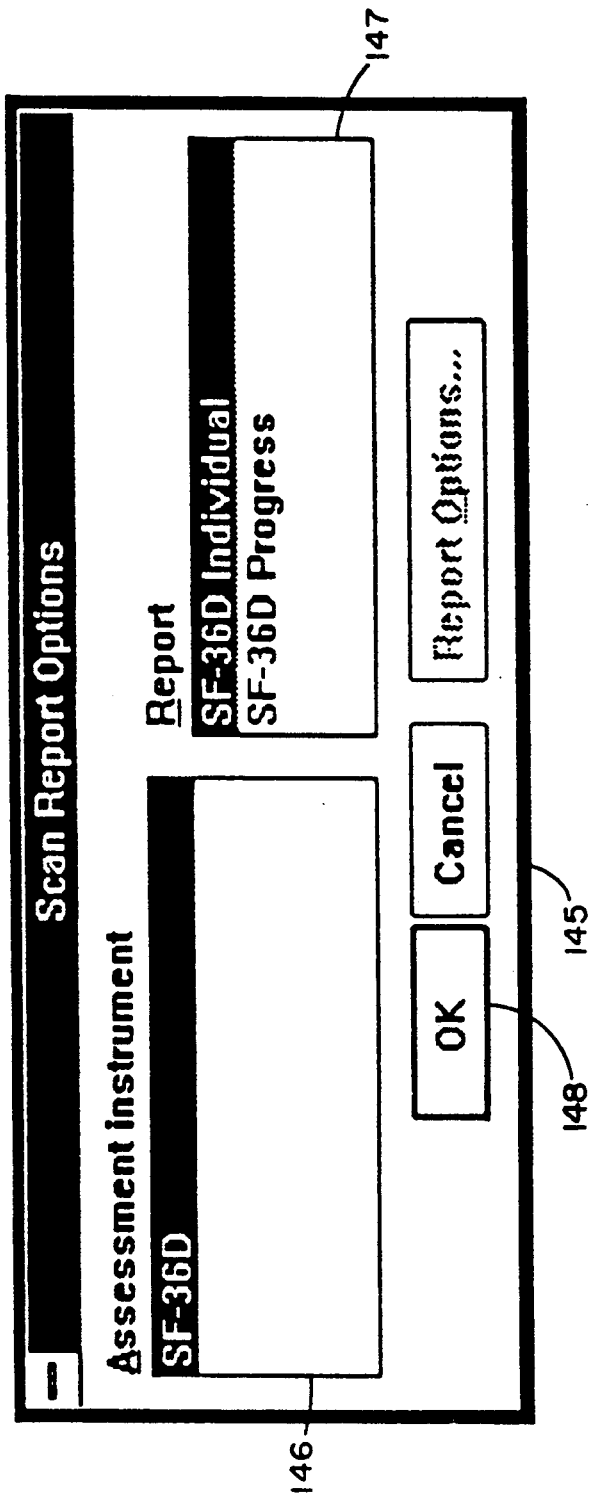
FIG. 23 represents a preferred user interface for selecting scan report options.
Figure 24:
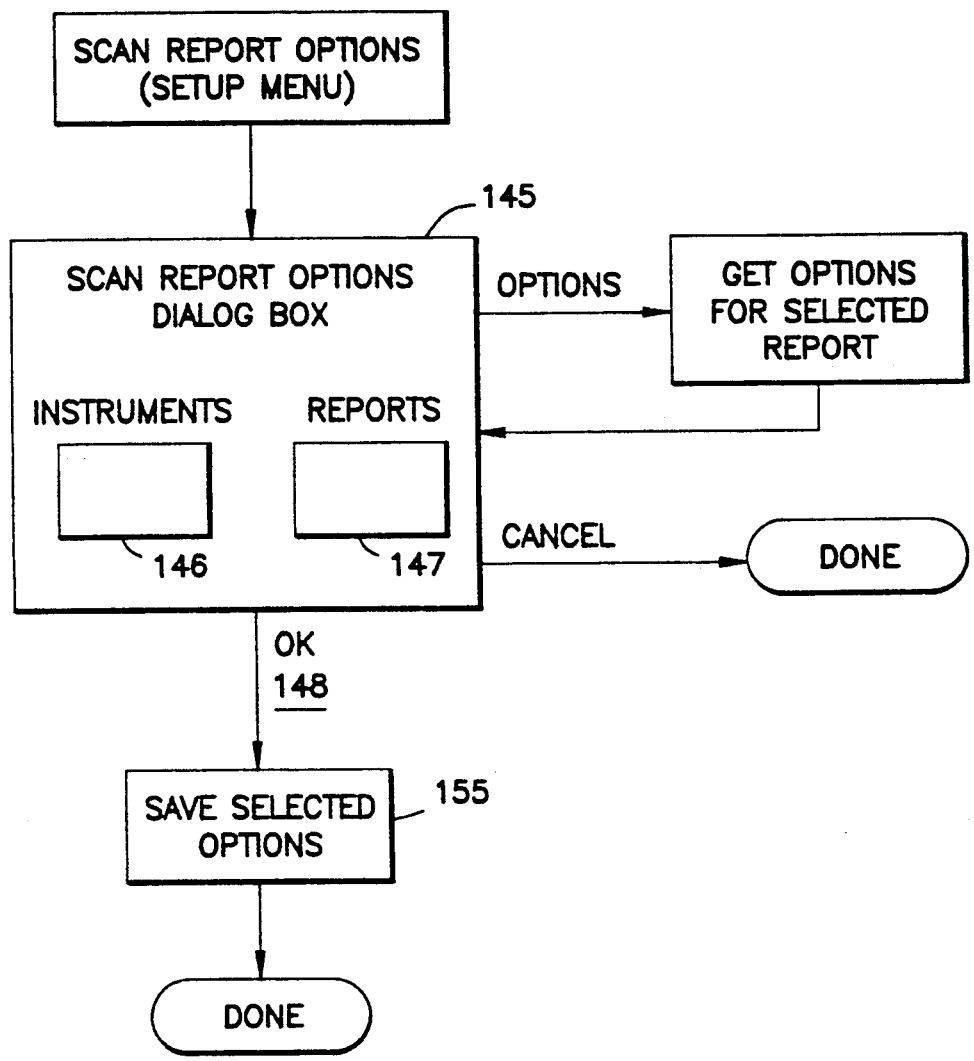
FIG. 24 represents a preferred flow of data through a process of selecting a scan report option.

Setup Menu 112 in Patient Manager Window 108 of the preferred system allows the user to control the system's configuration. For example, a preferred system will allow the user to select which reports are to be auto printed for each assessment when scanned. The system may be configured to present the user with a window 145 as shown in FIG. 23 for the purpose of allowing the user to select report options, the preferred flow of data of which is shown in FIG. 24. Window 146 in FIG. 23 displays the available assessment instruments, and window 147 displays the available reports for the assessment instrument selected in window 146. The user may select assessments and the desired reports for those assessments. When the user selects OK button 148, a preferred system stores the selected options at step 155.

Figure 25:
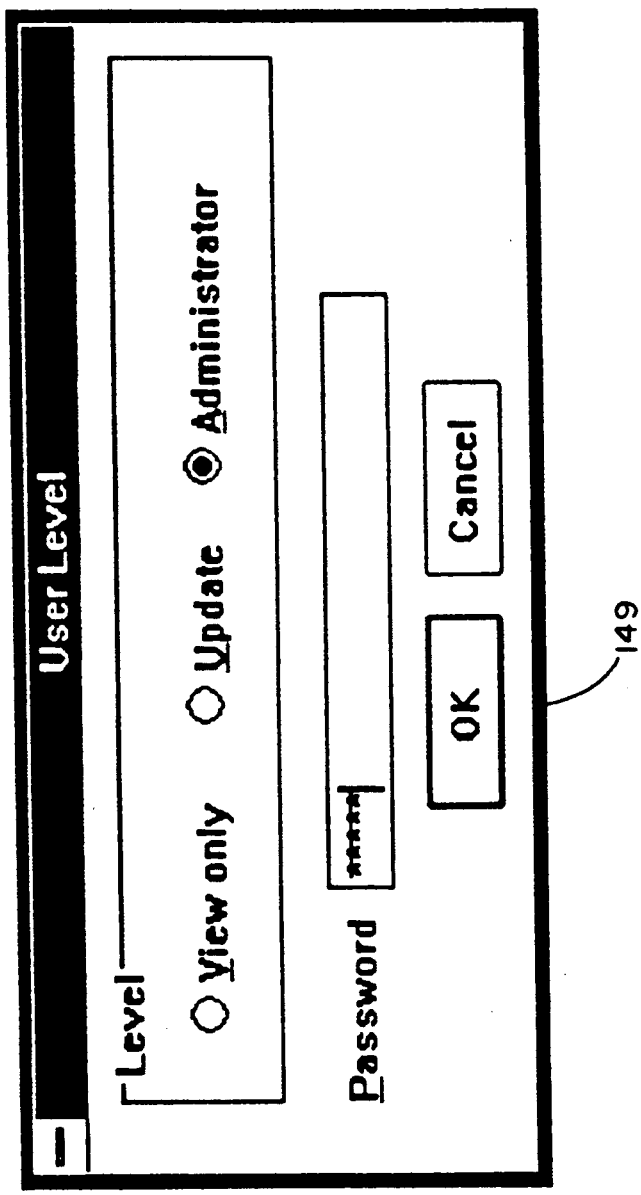
FIG. 25 represents a preferred user interface for entering a user level.
Figure 26:
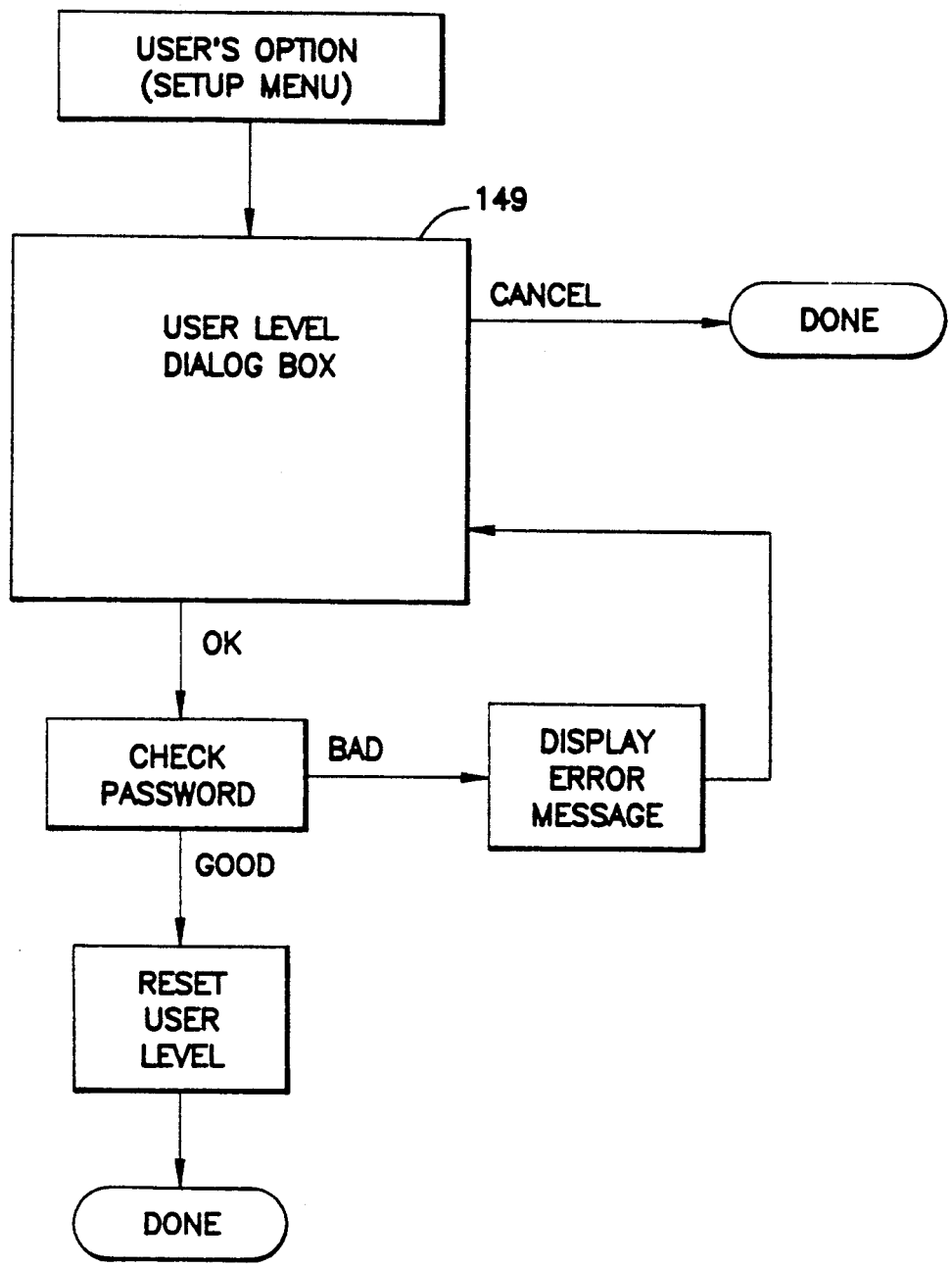
FIG. 26 represents a preferred flow of data through a process of setting up a user level.

The Setup Menu 112 of the preferred system provides the capability to establish user levels. The system may be configured to present the user with a window 149 as shown in FIG. 25 for the purpose of establishing user levels, the preferred flow of data of which is shown in FIG. 26. The user level determines which operations may be performed by a particular user. The system controls the menu options presented to a user depending upon the user level. The menu options presented to the user control which operations the user may perform. This is useful, for example, for security reasons and for maintaining confidentiality of sensitive patient information managed by the system.

There are three user levels in the preferred system. These user levels may be defined as shown in Table 3. If a user has the correct password, then the user may change user levels regardless of the current user level.

TABLE 3

| USER LEVEL | OPERATIONS AVAILABLE |
|---|---|
| VIEW ONLY | User may access: (1) patient records in a read only status; and (2) the current configuration for reports. |
| UPDATE | User may access all system operations except that the user: (1) may not delete a patient |

TABLE 3-continued

| USER LEVEL | OPERATIONS AVAILABLE |
|---|---|
|  | record; (2) may not delete or move an assessment record; and (3) is restricted to altering the printer setup in the Setup Operations. |
| ADMINISTRATOR | User may access all system operations. |

C. Database Server Module

The preferred Database Server Module 101 interfaces the Patient Manager Module 100 with a database. The Database Server performs various high level functions in the database, such as the functions referenced on the various figures that show the preferred flow of data for the Patient Manager operations described above. The preferred Database Server makes use of a commercial database manager, Btrieve, available from Novell, Inc.

The preferred system may be used either as a standalone system on a single machine or as a local area network ("LAN") system. In the preferred standalone system, the Patient Manager Module, Database Server, and Message File are all located on the same machine (see FIG. 1C). In the preferred LAN system, at least one Patient Manager Module is contained on each machine within the network. The Database Server in the preferred LAN system is located on its own machine, and the Message File resides on a shared network storage device so that the Database Server and each of the Patient Managers may access the Message File. In an alternate embodiment of the preferred LAN system, the Database Server operates on one of the machines containing a Patient Manager Module in what is known as a peer-to-peer system. In both the standalone and LAN preferred embodiments, the Database Server contains and manages the data files.

D. Report Generation Spooler Module

Figure 27:
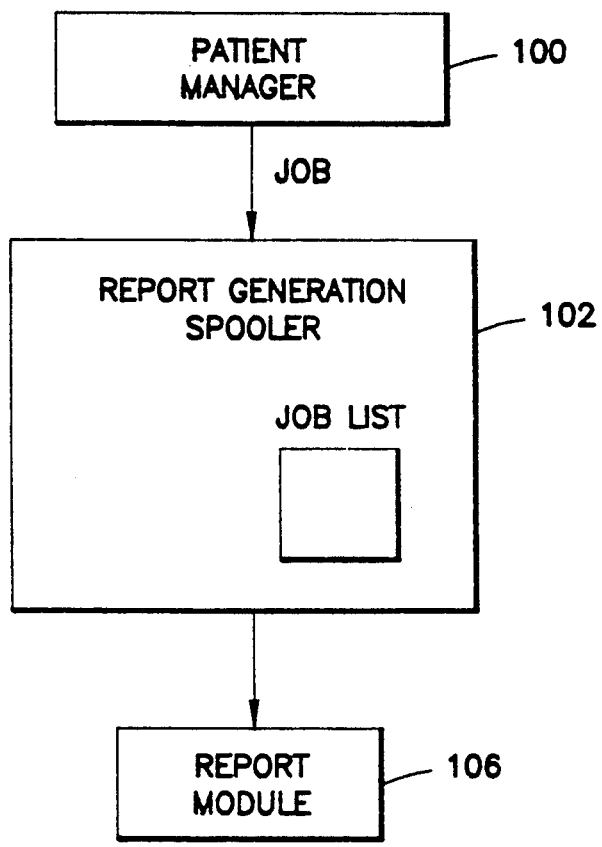
FIG. 27 represents a preferred flow of data through a Report Generation Spooler Module.

The preferred Report Generation Spooler Module 102 performs the function of receiving report jobs from the Patient Manager Module 100 and interfacing with the Report Module 106 to generate a report as a background process while the Patient Manager Module is operating. The preferred flow of data through the Report Generation Spooler Module is shown in FIG. 27 and may be defined by the pseudo code as shown in Table 4.

TABLE 4

| Pseudo code for Report Generation Spooler Module |
|---|
| WHILE more to do:<br>    GET next job from internal queue<br>    CALL Report Module to do next<br>        incremental step<br>    IF job was finished<br>        THEN remove from internal queue.<br>EXIT |

E. Report Module

The Report Module 106 preferably handles all report operations and may interact with the Report Generation Spooler Module 102 to generate reports for assessments. The Display Program Module, through the use of report executables, performs the necessary formatting requirements for the data of the various assessments. Examples of formatting assessments for reporting will be explained below.

III. Reporting and Display of Patient Assessment Histories

Figure 28:
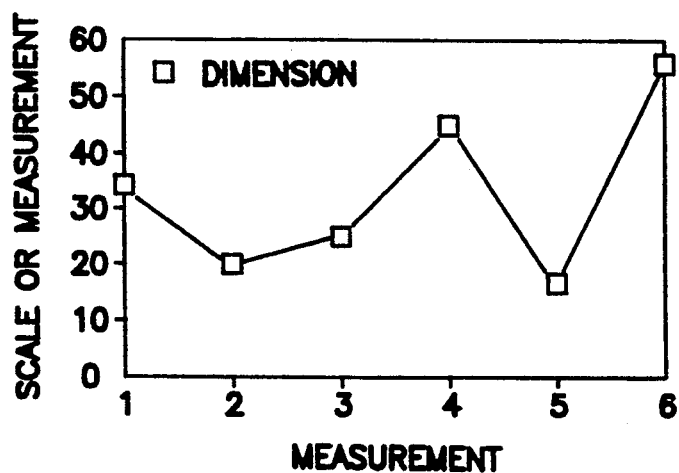
FIG. 28 shows a prior art method of displaying repeated administrations of a one-dimensional scale. The data are graphed using a traditional line graph method.
Figure 29:
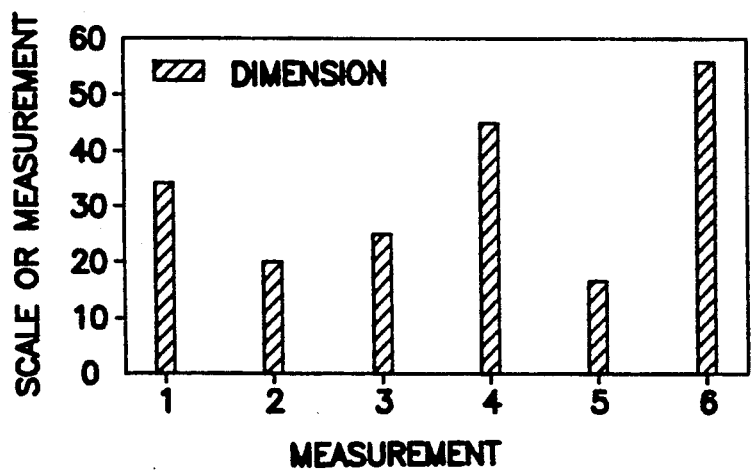
FIG. 29 shows a prior art method of displaying repeated administrations of a one-dimensional scale. The data are graphed using a traditional bar graph method.
Figure 30:
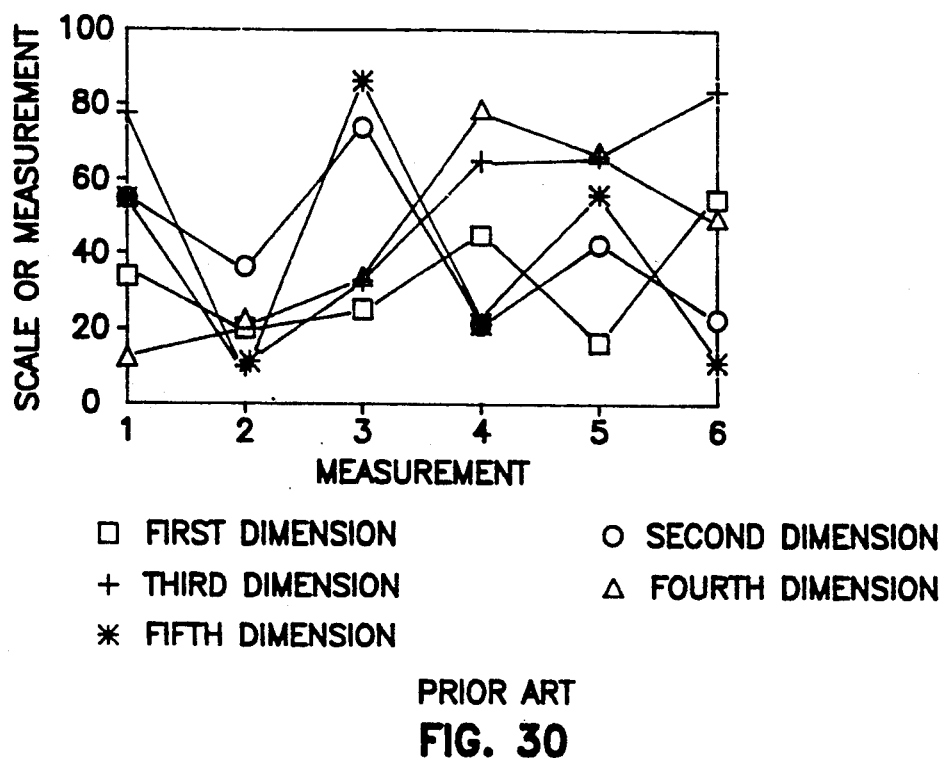
FIG. 30 shows a prior art method of displaying multiple administrations of a five-dimensional scale. The data are graphed using a traditional line graph method.
Figure 31:
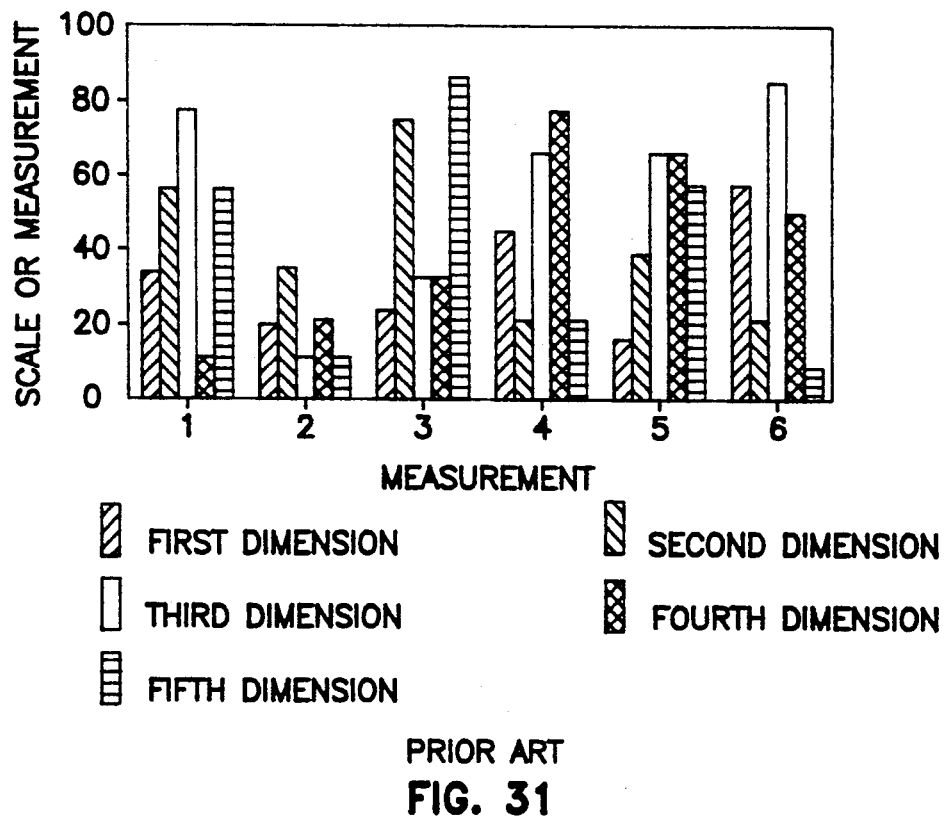
FIG. 31 shows a prior art method of displaying multiple administrations of a five-dimensional scale. The data are graphed using a traditional bar graph method.

A system which implements the three modules described above preferably includes a method of reporting the repeated administrations of multi-dimensional data in a manner that best facilitates visual analysis of the data. FIGS. 28 and 29 show prior art methods of displaying single administrations of multi-dimensional data. FIGS. 30 and 31 show prior art methods of displaying repeated administrations of multi-dimensional data. The repeated measures data normally comprises sets of data points, each data point having an x-value and a y-value. The typical prior art method of displaying one set of data is shown in FIGS. 28 and 29. This includes line or bar charts that use an arbitrary value for the baseline, which is usually the value of zero along the y-axis. When displaying multiple sets of repeated measures data, as shown in FIGS. 30 and 31, prior art methods include line and bar charts that use an arbitrary value for the baseline and further display all sets of data on one graph. These methods, however, may be visually confusing and difficult to interpret.

A preferred method of displaying repeated measures data is shown in FIGS. 32-38. This method displays each scale or dimension of a multi-dimensional assessment separately. For each scale or dimension, this method typically uses the y-value of the first data points as a baseline displayed as a line perpendicular to the y-axis and intersecting the y-axis at the y-value. The remaining data points are shown as a line graph plotted at intervals along the x-axis at points established by the x- and y-values of the remaining data points. This method allows a reader to quickly assess the data points relative to the first or baseline data point. For example, when the x-values comprise time occurrences, and the y-values comprise a measured parameter at each time occurrence, this method provides the reader with a display of data that shows how the measured parameter (y-values) changes over time with respect to the value of the first data point.

In the mental health field, the measured parameter may be an assessment of one aspect of a patient's personality as measured by an objective standard. The values of this parameter may be obtained by the results of a psychological test measuring several dimensions over many time occurrences. With personality assessments, this method provides the reader with objective analysis showing how each dimension of the patient's personality has changed over time with respect to the first value of each scale or dimension, which may have been taken when the patient began treatment. This method may, therefore, be used to track a patient's progress and the effectiveness of treatment by objectively showing whether the patient's condition has improved after beginning treatment.

Figure 32:
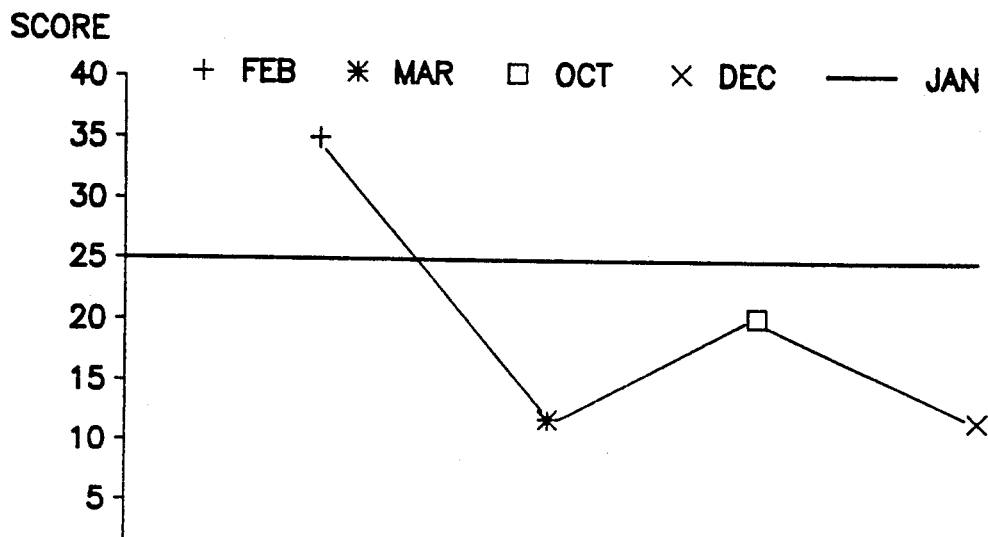
FIG. 32 shows a method of displaying one dimension measured repeatedly using the value of the first data point as the baseline and showing the x-axis time values as different symbols for each of the remaining data points.
Figure 33:
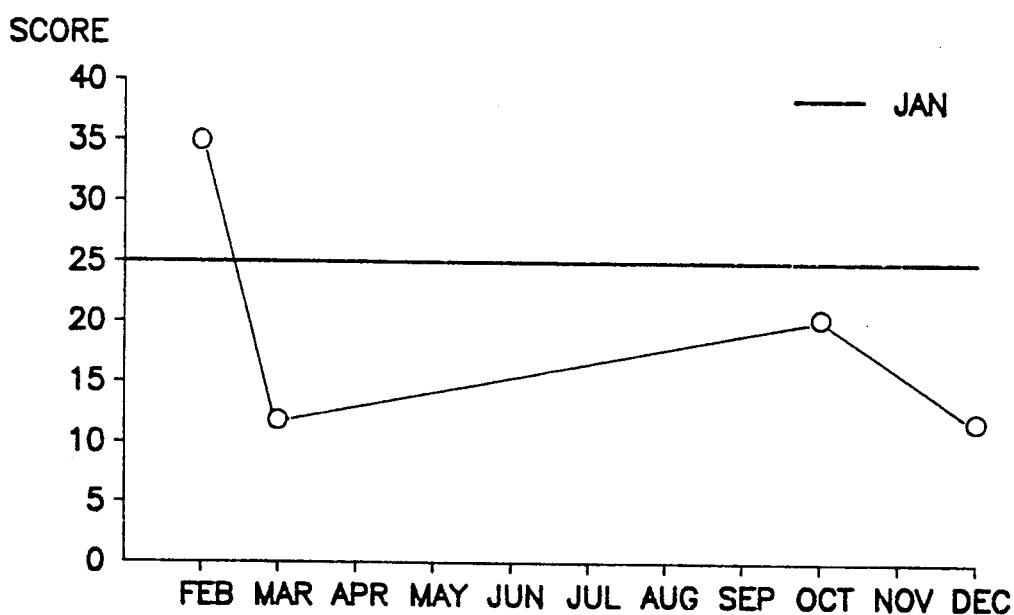
FIG. 33 shows a method of displaying one dimension measured repeatedly using the value of the first data point as the baseline and using constant time values for the x-axis.
Figure 34:
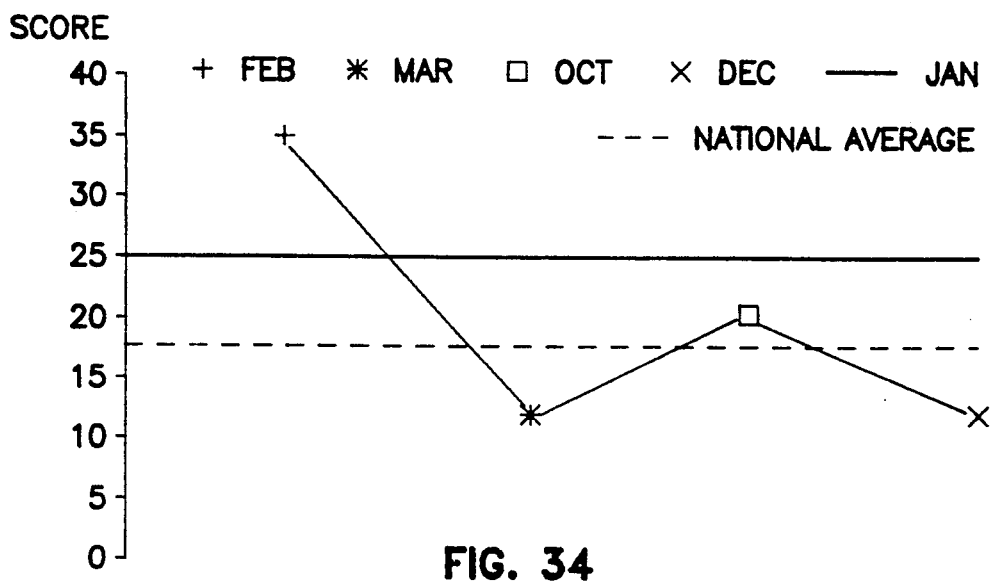
FIG. 34 shows a method of displaying one dimension measured repeatedly using the value of the first data point as a first baseline and further including a standard average value as a second baseline.
Figure 35:
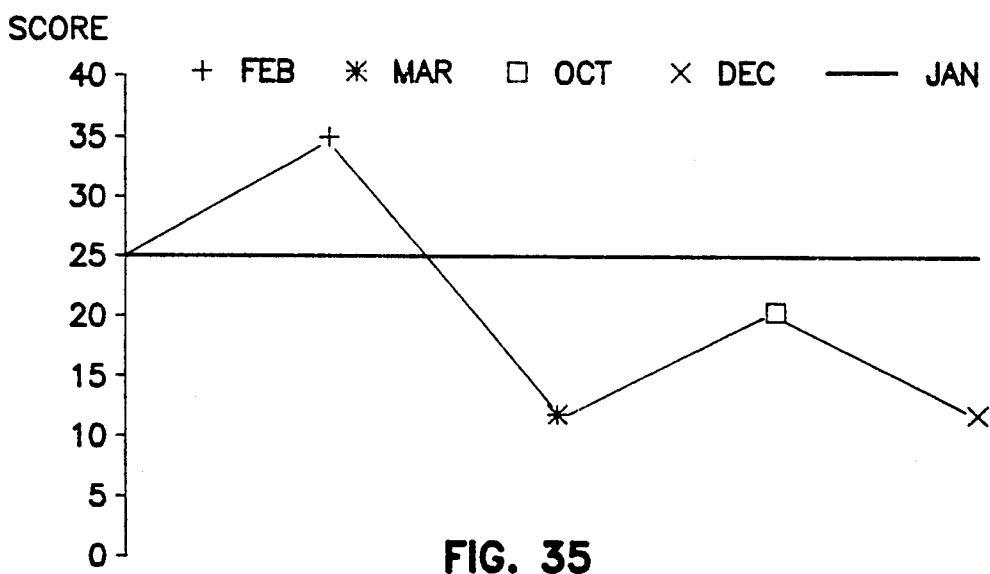
FIG. 35 shows a method of displaying one dimension measured repeatedly using the value of the first data point as a baseline, using constant time values for the x-axis, and connecting the second data point to the y-axis.

FIG. 32 is a graph that shows the x-axis time values as different symbols for each data point in addition to using the value of the first data point as the baseline. This graph shows the measure along the x-axis in equal increments regardless of the actual values and relies on the legend to communicate time differences. FIG. 33 is a graph that, in addition to showing the baseline that intersects the y-axis at the value of the first data point, shows the time values along an x-axis that crosses the y-axis at the zero point and graphs the x-axis itself using a constant scale. FIG. 34 is a graph that includes a standard value for one x-axis, such as the national average, in addition to showing a baseline x-axis that intersects the y-axis at the value of the first data point. FIG. 35 is a graph which shows that the second data point in the graph of FIG. 32 may be connected to the y-axis at the point at which the baseline crosses the y-axis as a method of displaying repeated measures data as described above.

Figure 36:
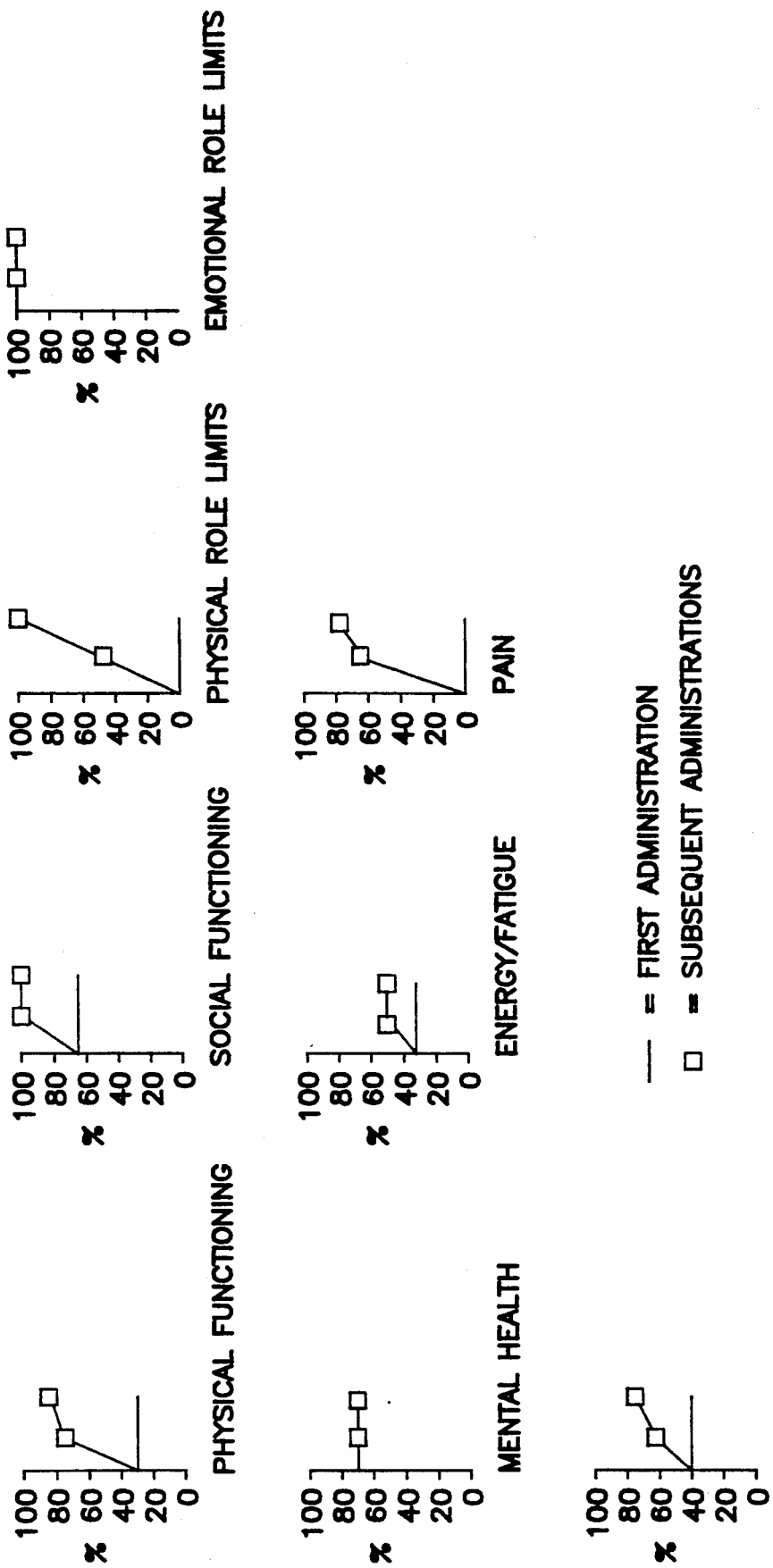
FIG. 36 shows a preferred method of displaying multidimensional repeated measures data by using the value of the first data point for each dimension as the baseline for a graph of that set.
Figure 37:
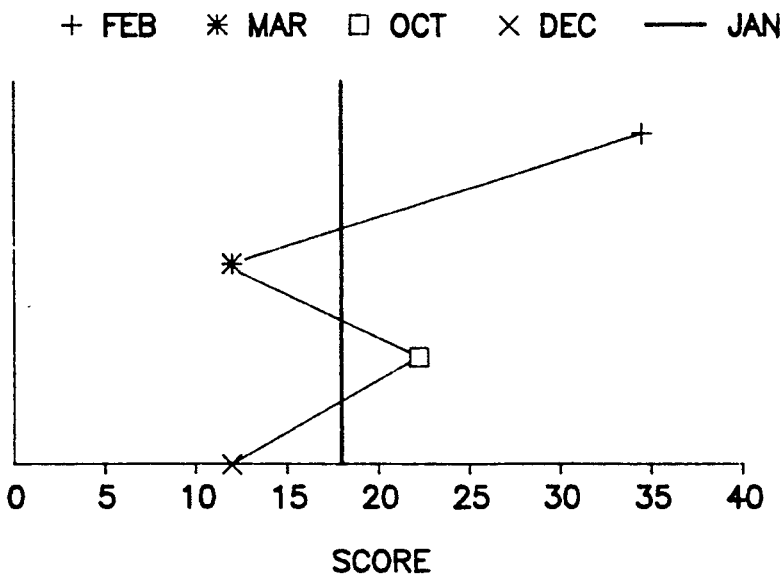
FIG. 37 shows a method of displaying one dimension measured repeatedly by reversing the axes in the method as shown in FIG. 32.
Figure 38:
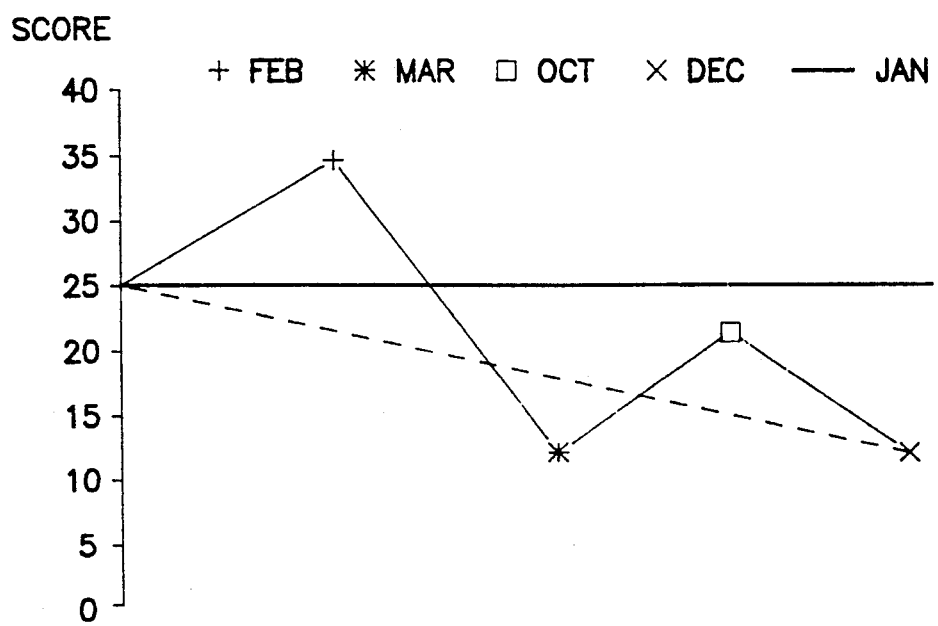
FIG. 38 shows a method of displaying repeated measures data using the method as shown in FIG. 32 and further including a regression line that connects the first data point with the last data point in the set of displayed data points.

The method of using the value of the first data point as the x-axis (baseline) may also be used for displaying multiple sets of repeated measures data together, a preferred method of which is shown in FIG. 36. Each set of repeated measures data is individually graphed, each representing a separate dimension of a multi-dimensional assessment, with the baseline of each set equal to the y-value of the first data point for the corresponding set. This method provides the reader with a representation of all the data that is visually easy to analyze and interpret. Each set of data readily shows how the data changes over time with respect to the first data point.

In the mental health field, for example, this method shows how each measured personality dimension of the patient has changed over time. Therefore, this method may be used with the preferred system described above for displaying test results from the Report Module so that a clinician may track a patient's progress and the effectiveness of the patient's treatment in each individual personality category of the patient.

While the present invention has been described in connection with the preferred embodiment thereof, it will be understood that many modifications will be readily apparent to those skilled in the art, and this application is intended to cover any adaptations or variations thereof. For example, the method of displaying repeated measures data is typically shown as a graph with an x-axis equal to the y-value of the first data point. However, this method may also be used to reverse the axes and display the data on a graph where the y-axis is equal to the x-value of the first data point. Likewise, the preferred embodiment of the present invention is shown as operating from a C language implementation on a PC DOS-based hardware platform. One skilled in the art will recognize that other programming or hardware environments may be used without departing from the scope of the invention.

It is manifestly intended that this invention be limited only by the claims and equivalents thereof.

What is claimed is:

1. A method of displaying data points representing multiple administrations of one dimension on a graph having a y-axis and a baseline perpendicular to the y-axis, each data point having an x-value corresponding to a point along the baseline and a y-value corresponding to a point along the y-axis, the method comprising:
   a) providing on the y-axis a range of possible y-values using a scaling appropriate for the data points;
   b) plotting a first data point on the y-axis;
   c) establishing the baseline having a range of possible x-values;
   d) locating the baseline so that it crosses the y-axis at a point equal to the y-value of the first data point; and
   e) plotting the x- and y-values of the remaining data points using the x- and y-coordinates established by the scaling of the baseline and the y-axis;
   f) whereby the baseline establishes a visual reference from which the y-value deviations of data points plotted subsequent to the first data point can be compared.

2. The method of claim 1 wherein a constant y-value which represents a standard average is plotted as a line parallel with the baseline.

3. The method of claim 2, further including the step of connecting each of the data points to adjacent data points.

4. The method of claim 3, further including the step of connecting the first data point to a last plotted data point.

5. The method of claim 1 wherein the method is used for plotting multidimensional repeated measures data points on a plurality of graphs so that each dimension of the repeated measures data is plotted on a separate graph.

6. A method of displaying data points representing multiple administrations of one dimension on a graph having mutually perpendicular first and second axes, each data point having a first value corresponding to a point on the first axis and a second value corresponding to a point on the second axis, the method comprising:
   a) providing the first axis with a range of possible first values using a scaling appropriate for the first value data points;
   b) plotting an initial first value data point on the first axis;
   c) providing the second axis with a range of possible second values using a scaling appropriate for the second value data points;
   d) locating the second axis so that is crosses the first axis at a point equal to the first value of the initial data point; and
   e) plotting the first and second values of the remaining data points using the first and second coordinates established by the scaling of the first and second axes;
   f) whereby the second axis establishes a visual reference from which the first value deviation of data points plotted subsequent to the initial data point can be compared.

7. The method of claim 6 wherein a constant second value which represents a standard average is plotted as a line parallel with the first axis.

8. The method of claim 7, further including the step of connecting each of the data points to adjacent data points.

9. The method of claim 8, further including the step of connecting the first data point to a last plotted data point.

10. The method of claim 6 wherein the method is used for plotting multidimensional repeated measures data points on a plurality of graphs so that each dimension of the repeated measures data is plotted on a separate graph.

11. A client-oriented, computer-implemented system for client assessment information management, comprising:
   a) input means for entering data, the input means comprising:
   i) client input means for entering client identification information; and
   ii) data processing means for receiving first and second sets of assessment information, comprising raw measurement data, obtained from first and second different types of measurement tools and for storing the first and second sets of assessment information in first and second sets of corresponding assessment records, the data processing means comprising: first assessment processing means for processing the first set of assessment information according to a first set of assessment processing rules; and second assessment processing means for processing the second set of assessment information according to a second set of assessment processing rules;
   b) client management means for organizing the data, the client management means comprising:
   i) client list means, responsive to the client input means, for organizing the client identification information into a list of client records so that each identified client is assigned at least one client record;
   ii) assessment list means, responsive to the data processing means, for organizing the first and second sets of assessment information into a list of assessment records; and
   iii) logical association means for logically associating at least one of the assessment records with at least one of the client records; and
   c) interpretation means for generating an interpretive report of the data, the interpretation means comprising: first report generation means for interpreting the first set of assessment information according to a first set of assessment reporting rules in order to generate a report of the first set of assessment information, the first set of assessment reporting rules comprising reporting functions tailored to the first type of measurement tool; and second report generation means for interpreting the second set of assessment information according to a second set of assessment reporting rules in order to generate a report of the second set of assessment information, the second set of assessment reporting rules comprising reporting functions tailored to the second type of measurement tool.

12. The system of claim 11 wherein the data processing means and the interpretation means comprise dynamic link library means for administrating and reporting the first and second sets of assessments, the dynamic link library means comprising a plurality of functions assessed and utilized by the data processing means and the interpretation means in order to process and report the data according the assessment processing rules and the assessment reporting rules.

13. The system of claim 11 wherein the data processing means further comprises means for entering a subjective narrative which characterizes the client.

14. The system of claim 11 wherein the logical association means comprises client record association means for organizing the client records into a sequential list.

15. The system of claim 11 wherein the client input means further comprises means for entering at least one of a client name, client identification number, and a client birth date.

16. The system of claim 11 wherein the client management means further comprises search and retrieve means for searching the list of client records for a client record containing the identification information for a particular client.

17. The system of claim 11 wherein the client management means further comprises update means for changing the client identification information in a particular client record.

18. The system of claim 11 wherein the client management means further comprises delete means for removing a client record from the list of client records.

19. The system of claim 11 wherein the client management means further comprises add record means for adding a new client record to the list of client records.

20. The system of claim 11 wherein the client management means further comprises assessment delete means for removing an assessment record from the list of assessment records.

21. The system of claim 11 wherein the data processing means further comprises scanning means for optically entering at least one of the first and second sets of assessment information.

22. The system of claim 21 wherein the data processing means further comprises verification means for verifying at least one of the first and second sets of assessment information before the assessment information is entered into at least one of the assessment records.

23. The system of claim 21 wherein the interpretation means further comprises automatic report generation means for automatically generating user-selected reports of scanned assessment information.

24. The system of claim 22 wherein the verification means further comprises add means for entering the verified assessment information into at least one of the assessment records.

25. The system of claim 11 wherein the client management means further comprises delete means for removing an assessment record from the list of assessment records.

26. The system of claim 11 wherein the data processing means further comprises means for entering a set of data points which can be plotted on an x-y graph where each data point has an x-value and a y-value.

27. The system of claim 26 wherein the interpretation means comprises display means for formatting the data points into a graphical report, the graphical report comprising:
   a) a y-axis having a range of possible y-values using a scaling appropriate for the data points;
   b) a first data point plotted on the y-axis;
   c) a baseline, perpendicular to the y-axis, having a range of possible x-values;
   d) whereby the baseline is located so that it crosses the y-axis at a point equal to the y-value of the first data point; and
   e) x- and y-values of the remaining data points plotted using the x- and y-coordinates established by the scaling of the baseline and the y-axis;
   f) whereby the baseline establishes a visual reference from which the y-value deviations of data points plotted subsequent to the first data point can be compared.

28. The system of claim 11 wherein the data processing means comprises means for entering a set of data points which can be plotted on mutually perpendicular axes where each data point has a first value and a second value.

29. The system of claim 28 wherein the output means comprises display means for formatting the data points into a graphical report, the graphical report comprising:
   a) a first axis with a range of possible first values using a scaling appropriate for the first value data points;
   b) an initial first-value data point plotted on the first axis;
   c) a second axis having a range of possible second values using a scaling appropriate for the second value data points;
   d) whereby the second axis is located so that it crosses the first axis at a point equal to the first value of the initial data point; and
   e) the first and second values of the remaining data points plotted using the first and second coordinates established by the scaling of the first and second axes;
   f) whereby the second axis establishes a visual reference from which the first-value deviation of data points plotted subsequent to the initial data point can be compared.

30. The system of claim 11 wherein:
   a) the data processing means comprises means for selecting narrative text for a particular client based on the assessment processing rules; and
   the interpretation means comprises means for collating and formatting the narrative text into narrative reports describing the client's clinical profile.

31. The system of claim 11 wherein the client management means comprises user-level means for controlling which operations within the system are available to a user depending upon a user-level corresponding to the user.

32. The system of claim 11 wherein the client management means comprises:
   a) database interface means for interactively receiving data from a user and for issuing a request that a particular database operation be performed on the data; and
   b) database server means for receiving the request from the database interface means and for performing the requested database operation.

33. The system of claim 32 wherein:
   a) the database interface means comprises means for posting the request in a message file; and
   b) the database server means comprises means for receiving the request from the message file and for issuing a reply to the message file indicating a status of the requested operation.

34. A client-oriented, computer-implemented system for client assessment information management, comprising:
   a) input means for entering data, the input means comprising:
      i) client input means for entering client identification information; and
      ii) data processing means for receiving first and second sets of assessment information, comprising raw measurement data, obtained from first and second administrations of a measurement tool and for storing the first and second sets of assessment information in first and second sets of corresponding assessment records, the data processing means comprising assessment processing means for processing the first and second sets of assessment information according to a set of assessment processing rules;
   b) client management means for organizing the data, the client management means comprising:
      i) client list means, responsive to the client input means, for organizing the client identification information into a list of client records so that each identified client is assigned at least one client record;
      ii) assessment list means, responsive to the data processing means, for organizing the first and second sets of assessment information into a list of assessment records; and iii) logical association means for logically associating at least one of the assessment records with at least one of the client records; and c) interpretation means for generating an interpretive report of the data, the interpretation means comprising report generation means for interpreting the first and second sets of assessment information according to a set of assessment reporting rules in order to generate a report of the first and second sets of assessment information, the set of assessment reporting rules comprising reporting functions tailored to the measurement tool.

35. The system of claim 34 wherein the data processing means and the interpretation means comprise dynamic link library means for administrating and reporting the first and second sets of assessments, the dynamic link library means comprising a plurality of functions accessed and utilized by the data processing means and the interpretation means in order to process and report the data according the assessment processing rules and the assessment reporting rules.

36. The system of claim 34 wherein the data processing means further comprises means for entering a subjective narrative which characterizes the client.

37. The system of claim 34 wherein the logical association means comprises client record association means for organizing the client records into a sequential list.

38. The system of claim 34 wherein the client input means further comprises means for entering at least one of a client name, client identification number, and a client birth date.

39. The system of claim 34 wherein the client management means further comprises search and retrieve means for searching the list of client records for a client record containing the identification information for a particular client.

40. The system of claim 34 wherein the client management means further comprises update means for changing the client identification information in a particular client record.

41. The system of claim 34 wherein the client management means further comprises delete means for removing a client record from the list of client records.

42. The system of claim 34 wherein the client management means further comprises add record means for adding a new client record to the list of client records.

43. The system of claim 34 wherein the client management means further comprises assessment delete means for removing an assessment record from the list of assessment records.

44. The system of claim 34 wherein the data processing means further comprises scanning means for optically entering at least one of the first and second sets of assessment information.

45. The system of claim 44 wherein the data processing means further comprises verification means for verifying at least one of the first and second sets of assessment information before the assessment information is entered into at least one of the assessment records.

46. The system of claim 44 wherein the interpretation means further comprises automatic report generation means for automatically generating user-selected reports of scanned assessment information.

47. The system of claim 45 wherein the verification means further comprises add means for entering the verified assessment information into at least one of the assessment records.

48. The system of claim 34 wherein the client management means further comprises delete means for removing an assessment record from the list of assessment records.

49. The system of claim 34 wherein the data processing means further comprises means for entering a set of data points which can be plotted on an x-y graph where each data point has an x-value and a y-value.

50. The system of claim 49 wherein the interpretation means comprises display means for formatting the data points into a graphical report, the graphical report comprising:

a) a y-axis having a range of possible y-values using a scaling appropriate for the data points;
b) a first data point plotted on the y-axis;
c) a baseline, perpendicular to the y-axis, having a range of possible x-values;
d) whereby the baseline is located so that it crosses the y-axis at a point equal to the y-value of the first data point; and
e) x- and y-values of the remaining data points plotted using the x- and y-coordinates established by the scaling of the baseline and the y-axis;
f) whereby the baseline establishes a visual reference from which the y-value deviations of data points plotted subsequent to the first data point can be compared.

51. The system of claim 34 wherein the data processing means comprises means for entering a set of data points which can be plotted on mutually perpendicular axes where each data point has a first value and a second value.

52. The system of claim 51 wherein the interpretation means comprises display means for formatting the data points into a graphical report, the graphical report comprising:

a) a first axis with a range of possible first values using a scaling appropriate for the first value data points;
b) an initial first-value data point plotted on the first axis;
c) a second axis having a range of possible second values using a scaling appropriate for the second value data points;
d) whereby the second axis is located so that it crosses the first axis at a point equal to the first value of the initial data point; and
e) the first and second values of the remaining data points plotted using the first and second coordinates established by the scaling of the first and second axes;
f) whereby the second axis establishes a visual reference from which the first-value deviation of data points plotted subsequent to the initial data point can be compared.

53. The system of claim 34 wherein:
a) the data processing means comprises means for selecting narrative text for a particular client based on the assessment processing rules; and
b) the interpretation means comprises means for collating and formatting the narrative text into narrative reports describing the client's clinical profile.

54. The system of claim 34 wherein the client management means comprises user-level means for controlling which operations within the system are available to a user depending upon a user-level corresponding to the user.

55. The system of claim 34 wherein the client management means comprises:

a) database interface means for interactively receiving data from a user and for issuing a request that a particular database operation can be performed on the data; and b) database server means for receiving the request from the database interface means and for performing the requested database operation.

56. The system of claim 55 wherein:

a) the database interface means comprises means for posting the request in a message file; and b) the database server means comprises means for receiving the request from the message file and for issuing a reply to the message file indicating a status of the requested operation.

* * * * *